(12) United States Patent
Pande et al.

(10) Patent No.: US 8,604,204 B2
(45) Date of Patent: Dec. 10, 2013

(54) FLUORESCENT DYES

(71) Applicant: Enzo Life Sciences, Inc., New York, NY (US)

(72) Inventors: Praveen Pande, Holbrook, NY (US); Zaiguo Li, Little Neck, NY (US); Maciej Szczepanik, Mount Sinai, NY (US); Wayne Forrest Patton, Dix Hills, NY (US)

(73) Assignee: Enzo Life Sciences, Inc., Farmingdale, NY (US)

( * ) Notice: Subject to any disclaimer, the term of this patent is extended or adjusted under 35 U.S.C. 154(b) by 0 days.

(21) Appl. No.: 13/733,324

(22) Filed: Jan. 3, 2013

(65) Prior Publication Data

US 2013/0217059 A1 Aug. 22, 2013

Related U.S. Application Data

(60) Division of application No. 12/315,629, filed on Dec. 4, 2008, now Pat. No. 8,357,801, which is a continuation-in-part of application No. PCT/US2007/016581, filed on Jul. 24, 2007, which is a continuation-in-part of application No. 11/177,923, filed on Jul. 7, 2005, now Pat. No. 7,737,281, which is a continuation-in-part of application No. 11/137,771, filed on May 24, 2005, now Pat. No. 7,569,695.

(51) Int. Cl.
*C07D 417/02* (2006.01)
*C12Q 1/00* (2006.01)

(52) U.S. Cl.
USPC ............ 546/172; 435/4; 435/6; 435/7.2; 548/156

(58) Field of Classification Search
USPC ............ 546/172; 548/156; 435/4, 6, 7.2
See application file for complete search history.

(56) References Cited

U.S. PATENT DOCUMENTS 7,569,695 B2 * 8/2009 Xiang et al. ............... 546/270.1

* cited by examiner

*Primary Examiner* — Charanjit Aulakh
(74) *Attorney, Agent, or Firm* — Anna D. DiGabriele Petti, Esq.

(57) ABSTRACT

The present invention provides dyes, reactive dyes and labeled reagents that may be used in the detection or quantification of desirable target molecules, such as proteins, nucleic acids and cellular organelles. Dyes are provided that may be used free in solution where the binding of the dye to the target molecule provides signal generation. Dyes are also provided that comprise reactive groups that may be used to attach the dyes to probes that will bind to desirable target molecules. The novel dyes of the present invention have been modified to provide beneficial properties.

20 Claims, 14 Drawing Sheets

CELLS STAINED WITH DYE 1

BRIGHT FIELD

GREEN FITC CHANNEL

CELLS STAINED WITH DYE 2

BRIGHT FIELD

TEXAS RED CHANNEL

CELLS STAINED WITH DYE 3

BRIGHT FIELD

TEXAS RED CHANNEL

CELLS STAINED WITH DYE 4

BRIGHT FIELD

GREEN FITC CHANNEL

CELLS STAINED WITH DYE 5

BRIGHT FIELD

DAPI CHANNEL

CELLS STAINED WITH DYE 6

BRIGHT FIELD

DAPI CHANNEL

CELLS STAINED WITH DYE 7

BRIGHT FIELD

TEXAS RED CHANNEL

CELLS STAINED WITH DYE 8

BRIGHT FIELD

TEXAS RED CHANNEL

CELLS STAINED WITH DYE 9

BRIGHT FIELD

TEXAS RED CHANNEL

| COMPOUND | Abs [nm] | Ex$^{DNA}$* [nm] | Em$^{DNA}$* [nm] | Ex$^{RNA}$* [nm] | Em$^{RNA}$* [nm] | EF$^{DNA}$# | EF$^{RNA}$# |
|---|---|---|---|---|---|---|---|
| DYE 10 | 494 | 507 | 523 | 504 | 526 | 350 | 420 |
| DYE 11 | 495 | 507 | 522 | 507 | 525 | 410 | 170 |
| DYE 12 | 500 | 507 | 524 | 507 | 530 | 220 | 470 |
| DYE 13 | 498 | 507 | 524 | 507 | 526 | 450 | 150 |

\* EXCITATION (Ex) AND EMISSION (Em) OF DYE/DNA OR DYE/RNA COMPLEX
EF – ENHANCEMENT OF FLUORESCENCE UPON BINDING OF THE DYE TO DNA OR
RNA AS COMPARED TO DYE ALONE

FIG. 10

CELLS STAINED WITH DYE 12

UNSTAINED CELLS

CELLS STAINED WITH DYE 12

CELLS STAINED WITH DYE 12

CELLS STAINED WITH DYE 10-12 & 14

LIGHT MIC.

FLUORESCENCE

COMPOSITE

EVALUATION OF DYES 10-12 AND 14 USED FOR CELLS STAINING OF FIXED HELA CELLS

| DYE | BRIGHTNESS | STABILITY | SELECTIVITY |
|---|---|---|---|
| DYE 10 | HIGH | LOW | NUCLEUS |
| DYE 11 | LOW | LOW | NUCLEUS + CYTOPLASM |
| DYE 12 | VERY HIGH | VERY GOOD | NUCLEUS |
| DYE 14 | LOW | FADES VERY FAST | CYTOPLASM + NUCLEUS |

FIG. 13

FLUORESCENT DYES

RELATED APPLICATIONS

This application is a continuation-in-part of U.S. patent application Ser. No. 11/137,771, filed May 24, 2005, published as US-2006-0269926-A1 on Nov. 30, 2006; it is also a continuation-in-part of U.S. patent application Ser. No. 11/177,923, filed on Jul. 7, 2005, published as US-2006-0269931-A1 on Nov. 30, 2006; and it is a continuation-in-part of U.S. Patent Application Serial No. PCT/US07/16581, filed on Jul. 24, 2007. This application claims priority to all three aforementioned applications.

FIELD OF THE INVENTION

This invention relates to field of labeling compositions, reagents and processes that are useful in applications related to the labeling, detection, quantification and localization of target molecules of interest that include nucleic acids and proteins. This invention also relates to methods and kits for identifying organelles or regions in cells of interest.

All patents, patent applications, patent publications, scientific articles and the like, cited or identified in this application are hereby incorporated by reference in their entirety in order to describe more fully the state of the art to which the present invention pertains.

BACKGROUND OF THE INVENTION

There are a variety of properties that might be desirable for dyes that are intended for use as markers for detection of proteins or nucleic acid hybridization. These can include the ability to bind to a protein, lipid or nucleic acid, the capability of incorporation into nucleic acids by enzymatic means when attached to a nucleotide, a lack of steric hindrance that could potentially interfere with hybridization, water solubility, lack of aggregation, ability to intercalate into double-stranded nucleic acids and the presence of a reactive group that allows attachment of the dye to a nucleotide or other desirable target. Suitable dyes could have many of these properties but do not need to have them all. For instance, the ability to intercalate may allow detection of hybridization events in the presence of unhybridized probes or it may provide increased hybridization stabilization. Examples of these applications are disclosed in European Patent Application EP 0 231 495, U.S. Pat. No. 5,994,056 and U.S. Pat. No. 6,174,670, all of which are incorporated by reference. Similarly, the ability to be incorporated by an enzyme is a useful property when carrying out enzymatic labeling of nucleic acids. Labels that are inhibitory towards incorporation can still be used in some methods where nucleic acids are chemically synthesized rather than using enzymatic means. Also, nucleotides with reactive groups such as allylamine may be incorporated enzymatically into nucleic acids and then in a second step they are post-synthetically modified by attachment of dyes. Steric hindrance may be compensated to some degree by the nature of the linker joining the dye to a nucleotide with regard to both the length and the constituents of the linker. For a discussion of this last point, see U.S. Patent Application Publication No. 2003/0225247, hereby incorporated by reference.

The particular spectral characteristics of dyes are also important qualities. Although broad-spectrum white light can be used as a source of excitation, lasers with defined set wavelengths are most commonly employed. As such, dyes that would find most immediate use would have excitation wavelengths that can make use of such laser emissions. Emission wavelengths are of a more flexible nature since filters can be used to isolate a particular part of the spectrum. However, it should be noted that there are a number of machines used for detection of labeled nucleic acids that have been designed with dyes that are commonly used. For instance, there are a number of slide scanners that have been optimized for detection of nucleic acids labeled with the Cy3 and Cy5 dyes described by Waggoner et al. in U.S. Pat. No. 5,268,486 (incorporated herein by reference). On the other hand, the availability of dyes that have useful properties but have wavelengths that are not commonly used can prove to be an incentive to adopt lasers with compatible wavelengths.

A set of dyes with well separated emission spectra may find use where more than one fluorophore is to be used at the same time. Well known applications in this are immunostaining for various proteins in cells, in situ hybridization for multiple targets, non-radioactive sequencing, nucleic acid array analysis, protein array analysis, as well as non-specific cellular staining with dyes having general affinities for proteins or lipids. On the other hand, overlapping spectral characteristics also have applications; for instance, emission by one fluorophore may be used to excite a second fluorophore through energy transfer when distances are sufficiently close.

Among the dyes that have been most widely used as markers for proteins and nucleic acid labeling are members of the xanthene, coumarin, symmetric and asymmetric cyanine dye families. See, for example, U.S. Patent Application Publication No. 2003/0225247; U.S. Pat. No. 5,696,157 and U.S. Pat. No. 5,830,912, all three of which are incorporated by reference.

A large number of useful dyes are based upon cyanine dyes. The general structure of cyanine dyes is as follows

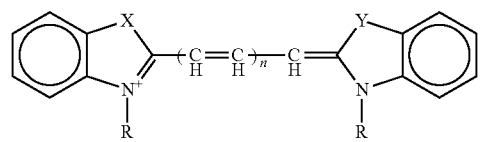

As will be discussed later, major factors in the particular spectral qualities of these dyes are dependent upon the number "n", the nature of "X" and "Y" and functional groups that extend the aromaticity of the dyes.

Other compounds that were functionally considered to be cyanine-type dyes (see U.S. Pat. No. 5,268,486 hereby incorporated by reference) are the styryl dyes whose general structure is:

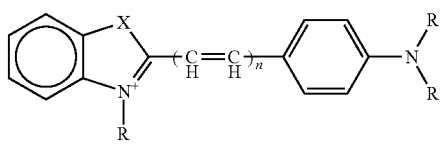

There are a variety of atoms that have been used in the X and Y positions. These have included carbon, sulfur, oxygen, nitrogen and selenium. When X or Y is a carbon, this portion of the dye is an indolinium moiety. When X or Y is substituted by sulfur, oxygen or nitrogen this portion is respectively described as a benzothiazolium, benzoxazolium or a benzimidazolium moiety.

Another version of styryl dyes can have picoline or quinoline moieties instead of the benzazolium group, thereby having the general structures:

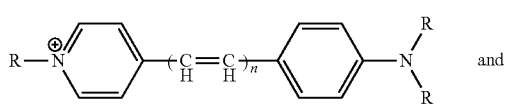

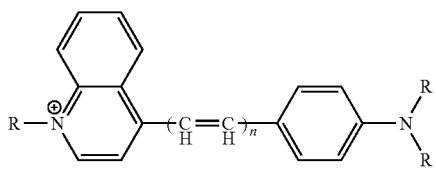

Asymmetric cyanine dyes contain one portion that is essentially the benzazolium portion of the cyanine dye family but connected to this portion by the methine bridge is a different aromatic compound. The aromatic moiety can be a six membered aromatic or heteroaromatic ring. Their general structure is as follows:

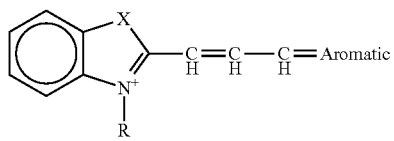

Improvements to these dyes have been carried out by substitution of various groups onto the basic structure, i.e. on the carbons and nitrogens of the preceding structures or where H or R groups are featured. Additionally, other rings may be fused to various parts of the rings in the structures above, thereby generating more complex structures. These modifications have led to shifts in the excitation and emission characteristics of the dyes that allow a large number of dyes with same basic structure but having different spectral characteristics, i.e. modifications can be made in their structure that can alter the particular wavelengths where these compounds will absorb and fluoresce light. As described above, the cyanine dyes can have a general structure comprising two benzazolium-based rings connected by a series of conjugated double bonds. The dyes are classified by the number (n) of central double bonds connecting the two ring structures; monocarbocyanine or trimethinecarbocyanine when n=1; dicarbocyanine or pentamethinecarbocyanine when n=2; and tricarbocyanine or heptamethinecarbocyanine when n=3. The spectral characteristics of the cyanine dyes have been observed to follow specific empirical rules. For example, each additional conjugated double bond between the rings usually raises the absorption and emission maximum about 100 nm. Thus, when a compound with n=1 has a maximum absorption of approximately 550 nm, equivalent compounds with n=2 and n=3 can have maximum absorptions of 650 nm and 750 nm respectively. Addition of aromatic groups to the sides of the molecules has lesser effects and may shift the absorption by 15 nm to a longer wavelength. The groups comprising the indolenine ring can also contribute to the absorption and emission characteristics. Using the values obtained with gem-dimethyl group as a reference point, oxygen substituted in the ring for the gem-dimethyl group can decrease the absorption and emission maxima by approximately 50 nm. In contrast, substitution of sulfur can increase the absorption and emission maxima by about 25 nm. R groups on the aromatic rings such as alkyl, alkyl-sulfonate and alkyl-carboxylate usually have little effect on the absorption and emission maxima of the cyanine dyes (U.S. Pat. No. 6,110,630, hereby incorporated by reference).

As described above, alteration of spectral qualities is only one useful modification that can be made to a dye. In another instance, modification of a dye by a sulfonate group may increase the stability of many dyes and thereby resist "bleaching" after illumination. Modification of dyes by sulfonation was later applied in the modification of cyanine dyes with reactive groups (U.S. Pat. No. 5,569,766 hereby incorporated by reference), where it was reported that the sulfonation decreases aggregation of labeled materials. It was further applied to xanthenes, coumarins and the non-benzazolium portion of asymmetric cyanine dyes (U.S. Pat. No. 5,436,134, U.S. Pat. No. 6,130,101 and U.S. Pat. No. 5,696,157, all of which are hereby incorporated by reference). Modifications of dyes haves also been made to increase their affinity or selectivity towards binding to nucleic acids (European Patent No. EP 0 231 495, U.S. Patent Application Publication No. 2003/0225247 and U.S. Pat. No. 5,658,751, all of which are incorporated by reference).

In many cases, the utility of these dyes has been achieved by synthesis of compounds with a reactive group that allows attachment of the dye to a target molecule. For instance, although cyanine dyes in themselves had been known for many years, it was only when derivatives were described with reactive groups (U.S. Pat. No. 5,268,486 hereby incorporated by reference) that they found widespread use in labeling proteins and nucleic acids. Their versatility was then increased by disclosure of other groups that could be used to attach cyanine dyes to suitable partners (U.S. Pat. No. 6,114,350 and U.S. Patent Application Publication No. 2003/0225247, both of which are hereby incorporated by reference). An exemplary list of electrophilic groups and corresponding nucleophilic groups that can be used for these purposes are given in Table 1 of U.S. Pat. No. 6,348,596 (hereby incorporated by reference).

A variety of linker arms may be used to attach dyes to targets. Commonly used constituents for linkers are chains that contain varying amounts of carbon, nitrogen, oxygen and sulfur. Examples of linkers using some of these combinations are given in U.S. Pat. No. 4,707,440, hereby incorporated by reference. Bonds joining together the constituents can be simple carbon-carbon bonds or they may be acyl bonds (U.S. Pat. No. 5,047,519), sulfonamide moieties (U.S. Pat. No. 6,448,008 B1) and polar groups (U.S. Patent Application Publication No. 2003/0225247) all of which are hereby incorporated by reference.

Among the targets sought to be detected in biological assays are cellular organelles and subcellular organelles. These have been the subject of various investigations. See, for example, U.S. patent application Ser. No. 12/231,988, filed on Sep. 8, 2008, the contents of which are incorporated by reference.

It would be helpful to develop other cyanine dye compounds which are useful for labeling target molecules of interest and which bind to specific cellular organelles or cell regions.

SUMMARY OF THE INVENTION

The present invention provides a novel compound comprising the structure:

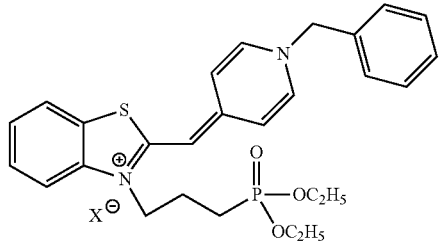

wherein X comprises an anion.

The present invention also provides a novel compound comprising the structure:

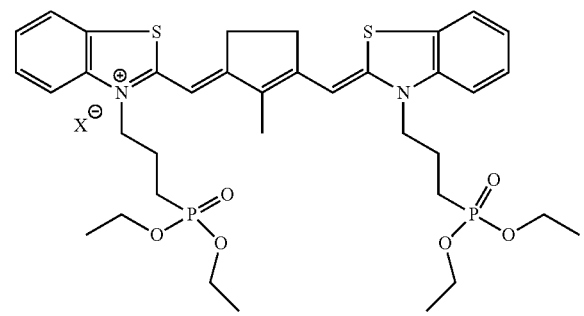

wherein X comprises an anion.

This invention further provides a novel compound comprising the structure:

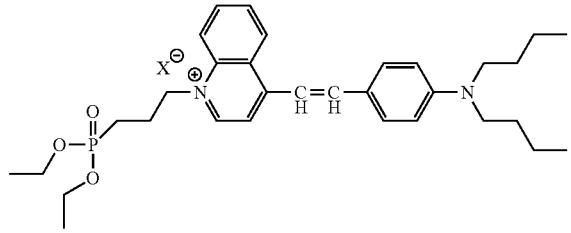

wherein X comprises an anion.

Also provided by the present invention is a novel compound comprising the structure:

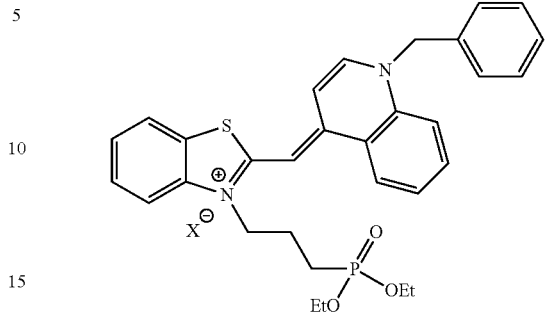

wherein X comprises an anion.

Additionally, this invention provides a novel compound comprising the structure:

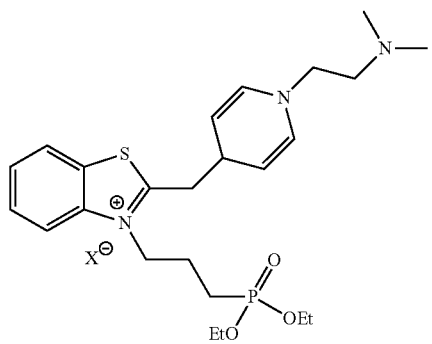

wherein X comprises an anion.

Another novel compound of this invention comprises the structure:

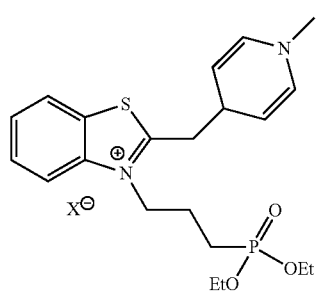

wherein X comprises an anion.

Another novel compound provided by the present invention comprises the structure:

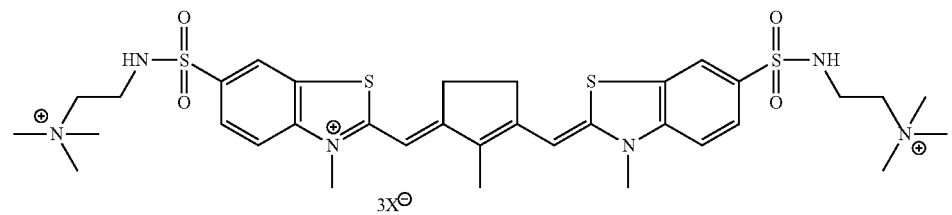

wherein X comprises an anion.

The present invention further provides a novel compound comprising the structure:

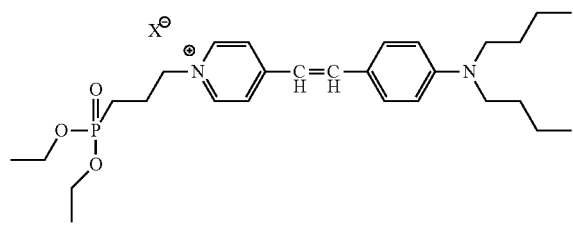

wherein X comprises an anion.

The present invention provides yet another novel compound comprising the structure:

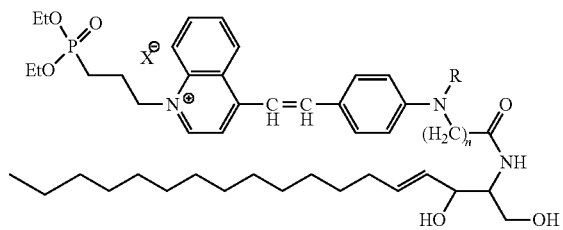

wherein X comprises an anion.

Also provided by the present invention is a novel compound comprising the structure:

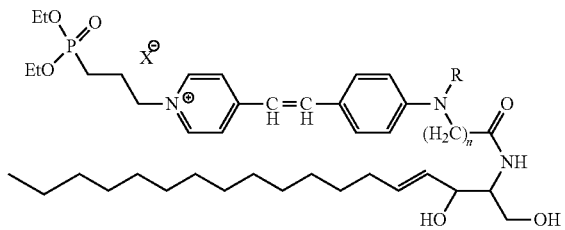

wherein X comprises an anion.

Yet another novel compound of this invention comprises the structure:

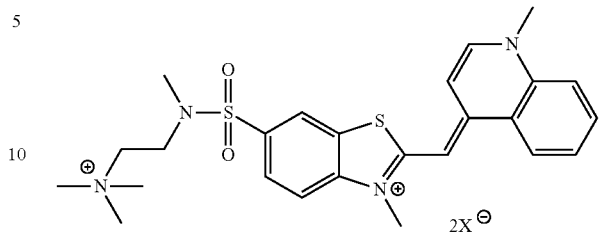

wherein X comprises an anion.

Still yet another novel compound of this invention comprises the structure:

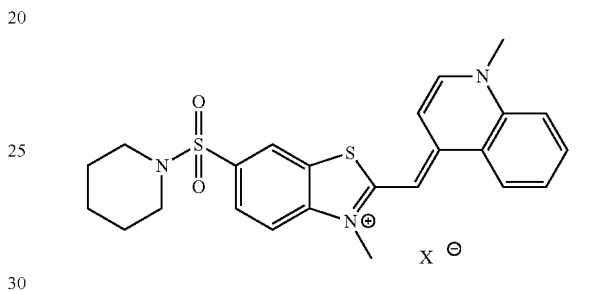

wherein X comprises an anion.

Additionally, the present invention provides a novel compound comprising the structure:

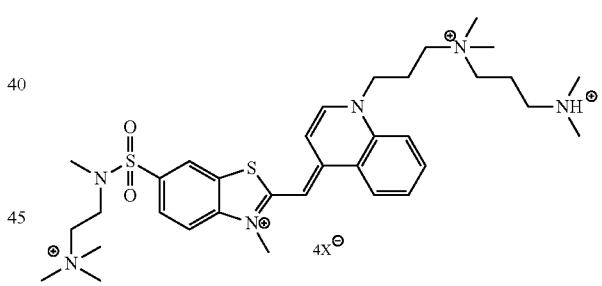

wherein X comprises an anion.

Further provided by this invention is a novel compound comprising the structure:

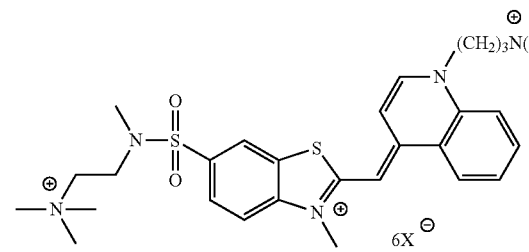

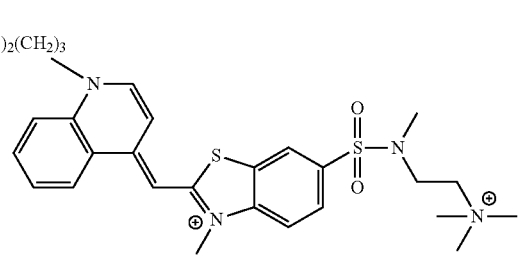

wherein X cmprises an anion.

Another novel compound provided by the present invention comprises the structure:

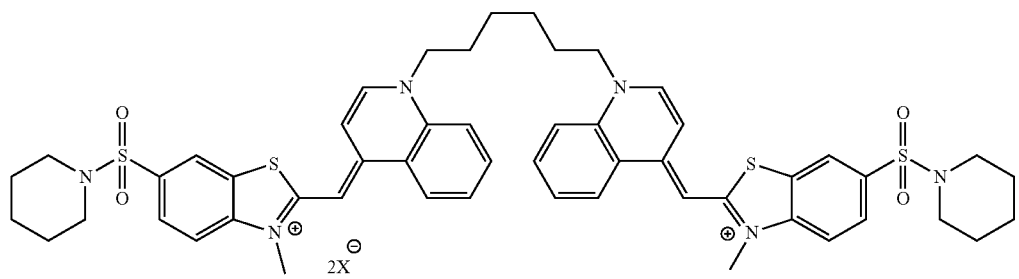 [SMILES: C[n+]1c(/C=C2\C=CN(CCCCCCN3C=C/C(=C\c4sc5cc(S(=O)(=O)N6CCCCC6)ccc5[n+]4C)c4ccccc43)c3ccccc32)sc2cc(S(=O)(=O)N3CCCCC3)ccc21]

wherein X comprises an anion.

The present invention also provides a method of labeling target molecules comprising the steps of (a) providing: (i) a sample containing such target molecules; and (ii) any of the novel compounds just described above, wherein the compound or compounds have been modified to comprise at least one reactive group; and (b) attaching any of the compound or compounds (ii) by means of the reactive group to the target molecules in the sample (i), thereby labeling the target molecules.

Also provided by this invention is a method for identifying specific organelles or regions in cells of interest comprising various steps. In the first step (A) there are provided (i) the cells of interest; and (ii) any of the compounds of aforementioned claims. In the next step (B), the cells of interest (i) are incubated with the compound (ii); after which the organelles or regions in the cells of interest are identified.

Further provided by this invention is a kit for identifying organelles or regions in cells of interest or in a sample containing cells of interest. The kit contains in packaged combination the following components or elements: (A) any of the aforementioned compounds, (B) optional buffers; and (C) instructions or a protocol for recommended use of the kit.

BRIEF DESCRIPTION OF THE FIGURES

FIG. 1A is a bright field image showing the cell morphology of a HeLa human cervical carcinoma cell line stained with Dye 1. FIG. 1B is the image of the same cells as in FIG. 1A that shows fluorescent nucleoli staining using green FITC channel.

FIG. 2A is a bright field image showing the cell morphology of a HeLa human cervical carcinoma cell line stained with Dye 2. FIG. 2B is the image of the same cells as in FIG. 2A that shows fluorescent nuclei staining using Texas red channel.

FIG. 3A is a bright field image showing mitochondrial staining of a HeLa human cervical carcinoma cell line with Dye 3. FIG. 3B is the image of the same cells as in FIG. 3A that shows fluorescence mitochondrial staining using Texas red channel.

FIG. 4A is a bright field image showing the cell morphology of a HeLa human cervical carcinoma line with Dye 4. FIG. 4B is the micrograph of FIG. 4A that has been imaged with a green FITC channel.

FIG. 5A is a bright field image showing the cell morphology of a HeLa human cervical carcinoma cell line stained with Dye 5. FIG. 5B is the image of the same cells as in FIG. 5A that shows fluorescent nucleoli staining using DAPI channel.

FIG. 6A is a bright field image showing the cell morphology of a HeLa human cervical carcinoma cell line stained with Dye 6. FIG. 6B is the image of the same cells as in FIG. 6A that shows fluorescent nucleoli staining using DAPI channel.

FIG. 7A is a bright field image showing the cell morphology of a HeLa human cervical carcinoma cell line stained with Dye 7. FIG. 7B is the image of the same cells as in FIG. 7A that shows fluorescent nuclei staining using Texas red channel.

FIG. 8A is a bright field image showing the cell morphology of a HeLa human cervical carcinoma cell line stained with Dye 8. FIG. 8B is the image of the same cells as in FIG. 8A that shows fluorescent staining of the cytoplasm using Texas red channel.

FIG. 9A is a bright field image showing the cell morphology of a HeLa human cervical carcinoma cell line stained with Dye 9 sphingosine conjugate. FIG. 9B is the image of the same cells as in FIG. 9A that shows fluorescent staining of Golgi bodies using Texas red channel.

FIG. 10 is a table that lists the spectral properties of Dyes 10-12 and 14 upon binding to nucleic acids.

FIG. 11A is an image showing unstained HeLa human cervical carcinoma cells. FIG. 11B is an image showing fluorescent nuclei staining of HelLa cells stained with Dye 12 using green channel. FIG. 11C is a composite of images shown in FIG. 11A and FIG. 11B.

FIG. 12A is an image showing fixed HeLa cells stained with Dyes 10-12 and 14 under a light microscope. FIG. 12B is an image showing fluorescent nuclei staining of HeLa cells stained with Dyes 10-12 and 14. FIG. 12C is a composite of the images shown in FIG. 12A and FIG. 12B.

FIG. 13 is a table evaluating Dyes 10-12 and 14 used for cell staining of fixed HeLa cells.

DESCRIPTION OF THE INVENTION

Figure 1A:
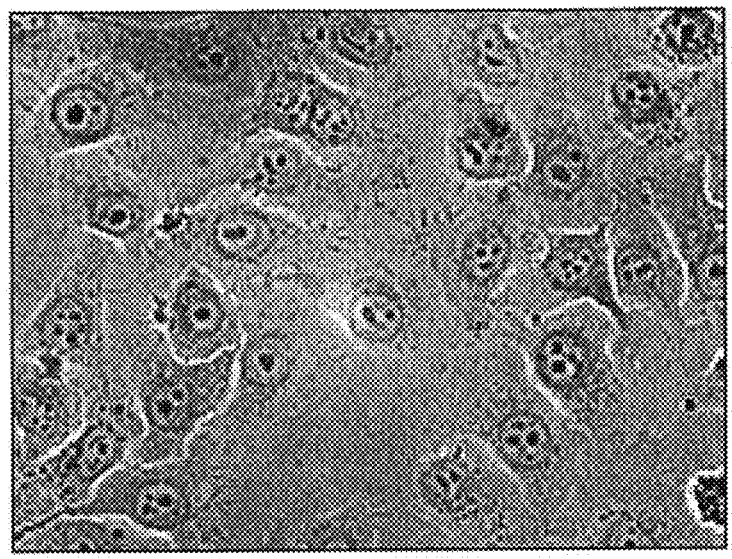
FIG. 1A-1B.

The present invention provides dyes and labeled reagents that may be used in the detection or quantification of desirable target molecules. Most of these dyes may be used free in solution where the binding of the dye to the target molecule provides increase fluorescence. Motivation for research in this area is drawn from needs for intracellular, tissue, and whole organism imaging. The present invention provides a family of cell-permeable organic probes that spontaneously localize to specific subcellular organelles, cell domains and cell regions which can be readily used in combination with other commonly used UV- and visible excitable organic fluorochromes and fluorescent proteins in multi-color imaging and detection applications. These organic probes can be used in concert with the other fluorochromes to report drug or compound effects in the dynamic context of the living whole cell.

The present dye series is based on cyanine chromophore that is modified by the addition of charged groups as exemplified by sulfonates, phosphates, phosphonates and their derivatives. Other dyes have been modified by the addition of polar groups such as sulfoxide, sulfone and sulfonamide moieties. Dyes may also be modified by both charged and polar groups.

In the present invention, sulfonates are considered to be any group with the formula $SO_3^-$ including both sulfonic acid as well as various sulfonate salts. The addition of a sulfonate group provides a charged moiety that can increase solubility, inhibit bleaching and reduce aggregation. The addition of phosphonate ($PO_3^=$), phosphate ($O-PO_3^=$) moieties or their derivatives may also provide such qualities. Transformation of the foregoing charged species into esters may convert a charged group into a polar group. Derivatives that may find use with the present invention can include thioanalogues such as thiophosphates, thiophosphonates and thioesters. Other derivatives that may find use can include phosphoramides and phosphonamides.

In the present invention, sulfones are considered to be any groups that have the formula $C-SO_2-C$ where carbon atoms are attached to the intervening sulfur atom. One of the carbon atoms may be part of a ring structure of the dye or it may part of an intervening alkyl group connecting the sulfone to the dye. When one of the carbons of a sulfone is replaced by a nitrogen atom the group is a sulfonamide.

The presence of the polar groups may help nucleotide incorporation since dyes with polar groups will be less negatively charged than their ionized equivalents and thus be less repelled by the negatively charged phosphate backbone of a nucleic acid template. The sulfone or sulfonamide group can be modified as desired by linkage to other moieties to add desirable properties. It is also understood that the degree of charge or polarity can be determined by the user by the addition of appropriate combinations of charged and polar groups to a dye.

In the present invention, Sulfoxides ($SOR^{13}$), Sulfones ($SO_2CR^{13}R^{14}R^{15}$) and sulfonamides sulfonamides ($SO_2NR^{13}R^{14}$) are respectively defined as having the general structures:

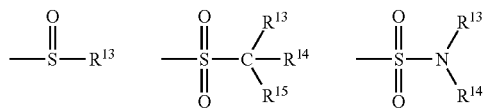

In the present invention, phosphates ($PO_4^=$), their monoesters ($PO_3^-E^{-R13}$), diesters ($PO_2ER^{13}ER^{14}$), are respectively defined as having the general structures:

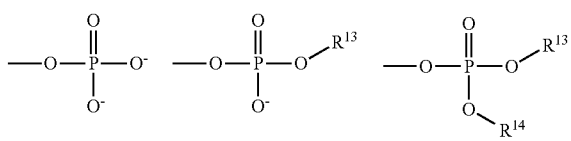

when E is an oxygen in the monoester and diester and

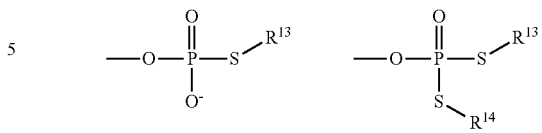

when E is a sulfur.

In the present invention, phosphonates ($PO_3^=$), their esters ($PO_2^-ER^{13}$ and $POER^{13}ER^{14}$) are respectively defined as having the general structures:

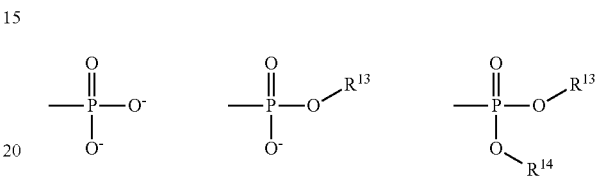

when E is an oxygen in the monoester and diester and

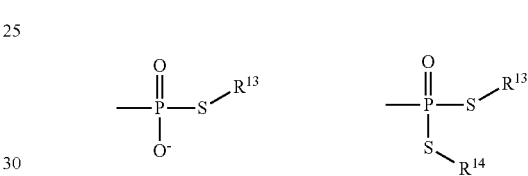

when E is a sulfur.

In the present invention, thiophosphates ($PSO_3^=$), their esters ($PSO_2^-ER^{13}$ and $PSOER^{13}ER^{14}$) are respectively defined as having the general structures:

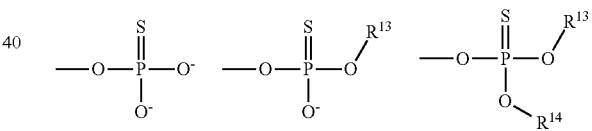

when E is an oxygen in the monoester and diester and

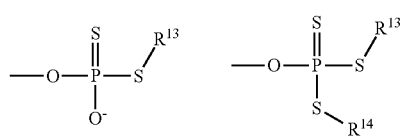

when E is a sulfur.

In the present invention, thiophosphonates ($PSO_2^=$), their esters ($PSO^-ER^{13}$ and $PSER^{13}ER^{14}$) are respectively defined as having the general structures:

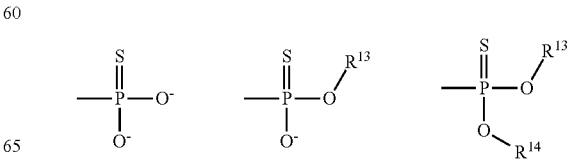

when E is an oxygen in the monoester and diester and

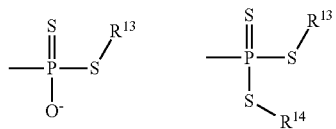

when E is a sulfur

In the present invention, sulfonates ($SO_3^-$), their esters ($SO_2ER^{13}$) are respectively defined as having the general structures:

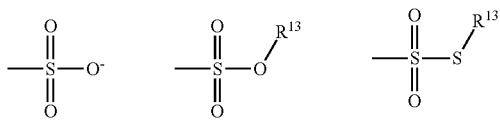

when E is an oxygen or sulfur in the ester linkage.

In the present invention, phosphonamides ($PONR^{13}R^{14}NR^{19}R^{20}$), phosphoramides ($PONR^{13}R^{14}NR^{15}NR^{19}R^{20}$) and phosphoramidites ($PO_2R^{19}NR^{13}R^{14}$) are respectively defined as having the general structures:

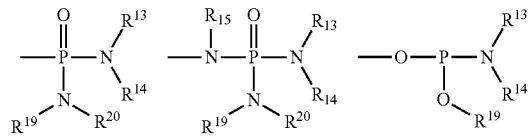

and their thioanalogues ($PSNR^{13}R^{14}NR^{19}R^{20}$), ($PSNR^{13}R^{14}NR^{15}NR^{19}R^{20}$) and ($POSR^{19}NR^{13}R^{14}$) having respectively the general structures:

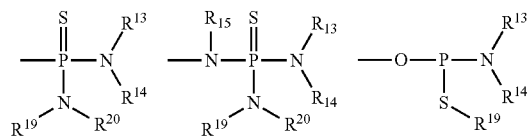

It is also understood that when a dye comprises anionic group, there will also be a cationic counterion present. Any cation may serve this purpose as long as it doesn't interfere with the use of the dye. Examples of cations that may serve as counterions can include but not be limited to hydrogen, sodium, potassium, lithium, calcium, cesium, ammonium, alkyl ammonium, alkoxy ammonium and pyridinium. It is also understood that when a dye comprises a cationic group, there will also be an anionic counterion present. Any anion may serve this purpose as long as it doesn't interfere with the use of the dye. Examples of anions that may serve as counterions can include but not be limited to halides such as a bromide, chloride, fluoride and iodide. Other examples can include but not be limited to perchlorate ($ClO_4^-$), sulfate ($SO_4^=$), sulfonate, alkane sulfonate, aryl sulfonate, phosphate, tosylate, mesylate and tetrafluoroborate moieties. In some cases the counterion or counterions are provided by the dye being a salt where they exist as separate ionic species. In other cases, the counterion or counterions may be present as part of the compound (sometimes called inner salts). It is understood that there may also be a combination of ions that are provided by the compound and salts. With regard to acid moieties that are shown in forms such as COOH it is also understood that these compounds may be found in ionized forms such as $COO^-$.

It should also be appreciated by those skilled in the art that the stoichiometric number of counterion or counterions which balance the charge or charges on the compound can be the same or they can be different provided that the counterions balance the charge(s) on the compound. The combination of counterions can be selected from any of the above mentioned anions. This applies for the combination of cations also.

It should be further appreciated by those skilled in the art that the foregoing descriptions of the anions and their stoichiometric number and/or combination are applicable to the compounds and dyes of the present invention, and to methods which use these compounds and dyes.

Alkyl or alkoxy R groups may be substituted or unsubstituted. Examples of substitutions can include but not be limited to one or more fluorine, chlorine, bromine, iodine, hydroxy, carboxy, carbonyl, amino, cyano, nitro or azido groups as well as other alkyl or alkoxy groups. The length of the alkoxy groups may be as desired. For instance, they may independently comprise from 1 to 18 carbons in length. They may be shorter as well, for instance they may be only 1 to 6 carbons in length in a dye molecule of the present invention.

The polar groups, charged groups and other substituents may be connected to the dye directly or they may be connected by a linker arm comprising carbon, nitrogen, sulfur, oxygen or any combination thereof. The linker arm may be saturated or unsaturated, linear or branched, substituted or unsubstituted as well as any combination of the foregoing.

In one aspect of the present invention, novel dyes that are based upon asymmetric cyanine dyes are disclosed. In one embodiment the dyes have the general structure:

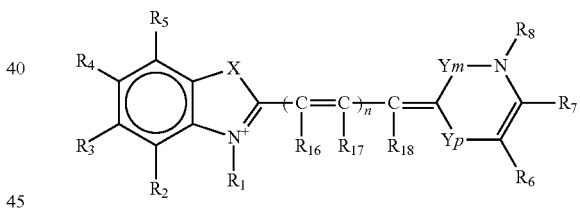

wherein X comprises $CR^{11}R^{12}$, $NR^{11}$, O, S or Se where $R^{11}$ and $R^{12}$ independently comprise hydrogen, a halogen, an amino group, an alkyl group wherein said alkyl group is saturated or unsaturated, linear or branched, substituted or unsubstituted, an alkoxy group wherein said alkyl group is saturated or unsaturated, branched or linear, substituted or unsubstituted, or when taken together, $R^{11}$ and $R^{12}$ form a 5 or 6 membered ring;

wherein n can be 0, 1, 2 or 3;

wherein Y is $-CR^9=CR^{10}-$;

wherein m and p can have values of 0 or 1 and m+p=1;

wherein at least one of $R^1$, $R^2$, $R^3$, $R^4$, $R^5$, $R^{11}$ or $R^{12}$ comprises Q(1) or at least one of $R^6$, $R^7$, $R^8$, $R^9$ or $R^{10}$ comprises Q(2);

wherein Q(1) comprises a sulfonate ($SO_3^-$), a sulfonate ester ($SO_2ER^{13}$), a sulfoxide ($SOR^{13}$), a sulfone ($SO_2CR^{13}R^{14}R^{15}$), a sulfonamide ($SO_2NR^{13}R^{14}$), a phosphate ($PO_4^=$), a phosphate monoester ($PO^-ER^{13}$), a phosphate diester ($PO_2ER^{13}ER^{14}$), a alkyl phosphonate ($PO_3^=$) a alkyl phosphonate monoester ($PO_2^-ER^{13}$) a alkyl phosphonate diester ($POER^{13}ER^{14}$), a thiophosphate ($PSO_3^=$), a thiophosphate monoester (PSO$_2^-$ER$^{13}$) a thiophosphate diester (PSOER$^{13}$ER$^{14}$), a thiophosphonate (PSO$_2^=$), a thiophosphonate monoester (PSO$^-$ER$^{13}$) a thiophosphonate diester (PSER$^{13}$ER$^{14}$), a phosphonamide (PONR$^{13}$R$^{14}$NR$^{19}$R$^{20}$), its thioanalogue (PSNR$^{13}$R$^{14}$NR$^{19}$R$^{20}$), a phosphoramide (PONR$^{13}$R$^{14}$NR$^{15}$NR$^{19}$R$^{20}$), its thioanalogue (PSNR$^{13}$R$^{14}$NR$^{15}$NR$^{19}$R$^{20}$), a phosphoramidite (PO$_2$R$^{19}$NR$^{13}$R$^{14}$) or its thioanalogue (POSR$^{19}$NR$^{13}$R$^{14}$) wherein any of E can independently comprise O or S and the structures are as described previously;

wherein Q is attached directly, or indirectly through a linker arm comprising carbon, sulfur, oxygen, nitrogen, and any combinations thereof and wherein said linker arm may be saturated or unsaturated, linear or branched, substituted or unsubstituted and any combinations thereof and wherein when Q is a sulfonamide, it does not comprise a terminal reactive group or a linker joining the dye to a target molecule;

wherein Q(2) comprises an alkyl, aminoalkyl, substituted aminoalkyl, a benzyl, a substituted benzyl, a sulfoxide (SOR$^{13}$), a sulfone (SO$_2$CR$^{13}$R$^{14}$R$^{15}$), a sulfonamide (SO$_2$NR$^{13}$R$^{14}$) a phosphate (PO$_4^=$), a phosphate monoester (PO$_3^-$ER$^{13}$), a phosphate diester (PO$_2$ER$^{13}$ER$^{14}$), a phosphonate (PO$_3^=$) a phosphonate monoester (PO$_2^-$ER$^{13}$) a phosphonate diester (POER$^{13}$ER$^{14}$), a thiophosphate (PSO$_3^=$), a thiophosphate monoester (PSO$_2^-$ER$^{13}$) a thiophosphate diester (PSOER$^{13}$ER$^{14}$), a thiophosphonate (PSO$_2^=$), a thiophosphonate monoester (PSO$^-$ER$^{13}$) a thiophosphonate diester (PSER$^{13}$ER$^{14}$), a phosphonamide (PONR$^{13}$R$^{14}$NR$^{19}$R$^{20}$), its thioanalogue (PSNR$^{13}$R$^{14}$NR$^{19}$R$^{20}$), a phosphoramide (PONR$^{13}$R$^{14}$NR$^{15}$NR$^{19}$R$^{20}$), its thioanalogue (PSNR$^{13}$R$^{14}$NR$^{15}$NR$^{19}$R$^{20}$), a phosphoramidite (PO$_2$R$^{19}$NR$^{13}$R$^{14}$) or its thioanalogue (POSR$^{19}$NR$^{13}$R$^{14}$) wherein any of E can independently comprise O or S and the structures are as described previously;

wherein Q(2) is attached directly, or indirectly through a linker arm comprising carbon, sulfur, oxygen, nitrogen, and any combinations thereof and wherein said linker arm may be saturated or unsaturated, linear or branched, substituted or unsubstituted and any combinations thereof and wherein when Q' is a sulfonamide, it does not comprise a terminal reactive group or a linker joining the dye to a target molecule;

wherein R$^{13}$, R$^{14}$, R$^{15}$, R$^{19}$ and R$^{20}$ can be hydrogen, a halogen, an amino group, an alkyl group wherein said alkyl group is saturated or unsaturated, linear or branched, substituted or unsubstituted, an alkoxy group wherein said alkoxy group is saturated or unsaturated, branched or linear, substituted or unsubstituted, or when taken together R$^{13}$ and R$^{14}$ form a five or six membered ring.

wherein R$^{13}$ and R$^{14}$ may further comprise a heteroatom containing side chain wherein said side chain is joined to the R group by a linkage which comprises an ether linkage (—OR$^{25}$), a thioether linkage (—SR$^{25}$), or an amine linkage (—NR$^{25}$R$^{26}$ or —N$^+$R$^{25}$R$^{26}$R$^{27}$), and wherein R$^{25}$, R$^{26}$ and R$^{27}$ independently comprise hydrogen, Z, an alkyl group wherein said alkyl group is saturated or unsaturated, linear or branched, substituted or unsubstituted, an alkoxy group that is saturated or unsaturated, branched or linear, substituted or unsubstituted, or when taken together, R$^{25}$ and R$^{26}$, and R$^{26}$ and R$^{27}$ independently comprise a five or six membered ring, and wherein any of R$^{25}$, R$^{26}$ or R$^{27}$ may further comprise said heteroatom containing side chain.

wherein R$^{16}$, R$^{17}$, R$^{18}$ and the remaining R$^1$, R$^2$, R$^3$, R$^4$, R$^5$, R$^6$, R$^7$, R$^8$, R$^9$, R$^{10}$, R$^{11}$ and R$^{12}$ can independently be hydrogen, Z, an alkyl group wherein said alkyl group is saturated or unsaturated, linear or branched, substituted or unsubstituted, an alkoxy group wherein said alkoxy group is saturated or unsaturated, branched or linear, substituted or unsubstituted, or when taken together, R$^2$ and R$^3$, R$^3$ and R$^4$, R$^4$ and R$^5$, R$^6$ and R$^7$, and R$^7$ and R$^8$ may form a 5 or 6 membered ring; or when taken together R$^1$ and R$^{16}$, R$^{11}$ and R$^{16}$, R$^{16}$ and R$^{17}$, R$^{17}$ and R$^{18}$, and R$^{18}$ and R$^9$ may form a 5 or 6 membered ring;

wherein Z comprises a carboxyl group (CO$_2$), a carbonate ester (COER$^{13}$), a sulfonate (SO$_3^-$), a sulfonate ester (SO$_2$ER$^{13}$), a sulfoxide (SOR$^{13}$), a sulfone (SO$_2$CR$^{13}$R$^{14}$R$^{15}$), a sulfonamide (SO$_2$NR$^{13}$R$^{14}$), a phosphate (PO$_4^=$), a phosphate monoester (PO$_3^-$ER$^{13}$), a phosphate diester (PO$_2$ER$^{13}$ER$^{14}$), a phosphonate (PO$_3^=$) a phosphonate monoester (PO$_2^-$ER$^{13}$) a phosphonate diester (POER$^{13}$ER$^{14}$), a thiophosphate (PSO$_3^=$), a thiophosphate monoester (PSO$_2^-$ER$^{13}$) a thiophosphate diester (PSOER$^{13}$ER$^{14}$), a thiophosphonate (PSO$_2^=$), a thiophosphonate monoester (PSO$^-$ER$^{13}$) a thiophosphonate diester (PSER$^{13}$ER$^{14}$), a phosphonamide (PONR$^{13}$R$^{14}$NR$^{19}$R$^{20}$), its thioanalogue (PSNR$^{13}$R$^{14}$NR$^{19}$R$^{20}$), a phosphoramide (PONR$^{13}$R$^{14}$NR$^{15}$NR$^{19}$R$^{20}$) its thioanalogue (PSNR$^{13}$R$^{14}$NR$^{15}$NR$^{19}$R$^{20}$), a phosphoramidite (PO$_2$R$^{19}$NR$^{13}$R$^{14}$) or its thioanalogue (POSR$^{19}$NR$^{13}$R$^{14}$) where E can be independently O or S and the structures are as described previously;

wherein Z is attached directly, or indirectly through a linker arm comprising carbon, sulfur, oxygen, nitrogen, and any combinations thereof and wherein said linker arm may be saturated or unsaturated, linear or branched, substituted or unsubstituted and any combinations thereof;

wherein any of R$^1$, R$^2$, R$^3$, R$^4$, R$^5$, R$^6$, R$^7$, R$^8$, R$^9$ or R$^{10}$, R$^{11}$ or R$^{12}$ may further comprise a heteroatom containing side chain wherein said side chain is joined to the R group by a linkage which comprises an ether linkage (—OR$^{25}$), a thioether linkage (—SR$^{25}$), or an amine linkage (—NR$^{25}$R$^{26}$ or —N$^+$R$^{25}$R$^{26}$R$^{27}$), and wherein R$^{25}$, R$^{26}$ and R$^{27}$ independently comprise hydrogen, Z, an alkyl group wherein said alkyl group is saturated or unsaturated, linear or branched, substituted or unsubstituted, an alkoxy group that is saturated or unsaturated, branched or linear, substituted or unsubstituted, or when taken together, R$^{25}$ and R$^{26}$, and R$^{26}$ and R$^{27}$ independently comprise a five or six membered ring, and wherein any of R$^{25}$, R$^{26}$ or R$^{27}$ may further comprise said heteroatom containing side chain, and wherein R$^8$ may comprise a substituted group capable of forming symmetric or asymmetric polymeric dye.

In the prior art, the non-benzazolium portion of asymmetric dyes has been modified with sulfonate groups (U.S. Pat. No. 5,436,134) but not the benzazolium portion as described in the present invention.

In another aspect of the present invention, novel dyes that are based upon styrene dyes are disclosed. In one embodiment the dyes have the general structure:

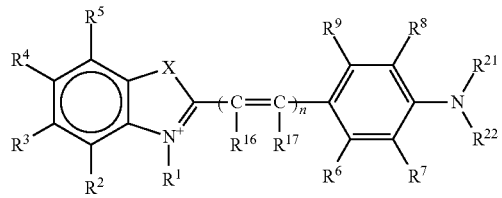

wherein X comprises CR$^{11}$R$^{12}$, NR$^{11}$, O, S or Se where R$^{11}$ and R$^{12}$ independently comprise hydrogen, a halogen, an amino group, an alkyl group wherein said alkyl group is saturated or unsaturated, linear or branched, substituted or unsubstituted, an alkoxy group wherein said alkyl group is saturated or unsaturated, branched or linear, substituted or unsubstituted, or when taken together, $R^{11}$ and $R^{12}$ form a 5 or 6 membered ring;

wherein n can be 1, 2 or 3;

wherein at least one of $R^1$, $R^2$, $R^3$, $R^4$, $R^5$, $R^6$, $R^7$, $R^8$, $R^9$, $R^{11}$, $R^{12}$, $R^{21}$ or $R^{22}$ comprises Q, wherein Q comprises a sulfoxide ($SOR^{13}$), a sulfone ($SO_2CR^{13}R^{14}R^{15}$), a sulfonamide ($SO_2NR^{13}R^{14}$), a phosphonate ($PO_3^=$), a phosphonate monoester ($PO_2^-ER^{13}$) a phosphonate diester ($POER^{13}ER^{14}$), a thiophosphate ($PSO_3^=$), a thiophosphate monoester ($PSO_2^-ER^{13}$) a thiophosphate diester ($PSOER^{13}ER^{14}$), a thiophosphonate ($PSO_2^=$), a thiophosphonate monoester ($PSO^-ER^{13}$) a thiophosphonate diester ($PSER^{13}ER^{14}$), a phosphonamide ($PONR^{13}R^{14}NR^{19}R^{20}$), its thioanalogue ($PSNR^{13}R^{14}NR^{19}R^{20}$), a phosphoramide ($PONR^{13}R^{14}NR^{15}NR^{19}R^{20}$), its thioanalogue ($PSNR^{13}R^{14}NR^{15}NR^{19}R^{20}$), a phosphoramidite ($PO_2R^{19}NR^{13}R^{14}$) or its thioanalogue ($POSR^{19}NR^{13}R^{14}$) wherein any of E can independently comprise O or S;

wherein Q is attached directly, or indirectly through a linker arm comprising carbon, sulfur, oxygen, nitrogen, or any combinations thereof and wherein said linker arm may be saturated or unsaturated, linear or branched, substituted or unsubstituted or any combinations thereof and wherein when Q(2) is a sulfonamide, it does not comprise a terminal reactive group or a linker joining the dye to a target molecule;

wherein $R^{13}$, $R^{14}$, $R^{15}$, $R^{19}$ and $R^{20}$ can be hydrogen, a halogen, an amino group, an alkyl group wherein said alkyl group is saturated or unsaturated, linear or branched, substituted or unsubstituted, an alkoxy group wherein said alkoxy group is saturated or unsaturated, branched or linear, substituted or unsubstituted, or when taken together $R^{13}$ and $R^{14}$ form a five or six membered ring;

wherein $R^{16}$, $R^{17}$ and the remaining $R^1$, $R^2$, $R^3$, $R^4$, $R^5$, $R^6$, $R^7$, $R^8$, $R^9$, $R^{11}$, $R^{12}$, $R^{16}$, $R^{17}$, $R^{21}$ and $R^{22}$ can independently be hydrogen, Z, an alkyl group wherein said alkyl group is saturated or unsaturated, linear or branched, substituted or unsubstituted, an alkoxy group wherein said alkoxy group is saturated or unsaturated, branched or linear, substituted or unsubstituted, or when taken together, $R^2$ and $R^3$, $R^3$ and $R^4$, $R^4$ and $R^5$, $R^6$ and $R^7$, $R^7$ and $R^8$, $R^1$ and $R^{16}$, $R^{11}$ and $R^{16}$, $R^{16}$ and $R^{17}$, $R^{17}$ and $R^{18}$, and $R^{18}$ and $R^9$ may form a 5 or 6 membered ring;

wherein Z comprises a carboxyl group ($CO_2^-$), a carbonate ester ($COER^{13}$), a sulfonate ($SO_3^-$), a sulfonate ester ($SO_2ER^{13}$), a sulfoxide ($SOR^{13}$), a sulfone ($SO_2CR^{13}R^{14}R^{15}$), a sulfonamide ($SO_2NR^{13}R^{14}$), a phosphate ($PO_4^=$), a phosphate monoester ($PO_3^-ER^{13}$), a phosphate diester ($PO_2ER^{13}ER^{14}$) a phosphonate ($PO_3^=$) a phosphonate monoester ($PO_2^-ER^{13}$) a phosphonate diester ($POER^{13}ER^{14}$), a thiophosphate ($PSO_3^=$), a thiophosphate monoester ($PSO_2^-ER^{13}$) a thiophosphate diester ($PSOER^{13}ER^{14}$), a thiophosphonate ($PSO_2^=$), a thiophosphonate monoester ($PSO^-ER^{13}$) a thiophosphonate diester ($PSER^{13}ER^{14}$), a phosphonamide ($PONR^{13}R^{14}NR^{19}R^{20}$), its thioanalogue ($PSNR^{13}R^{14}NR^{19}R^{20}$), a phosphoramide ($PONR^{13}R^{14}NR^{15}NR^{19}R^{20}$), its thioanalogue ($PSNR^{13}R^{14}NR^{15}NR^{19}R^{20}$), a phosphoramidite ($PO_2R^{19}NR^{13}R^{14}$) or its thioanalogue ($POSR^{19}NR^{13}R^{14}$) where E can be independently O or S;

wherein Z is attached directly, or indirectly through a linker arm comprising carbon, sulfur, oxygen, nitrogen, and any combinations thereof and wherein said linker arm may be saturated or unsaturated, linear or branched, substituted or unsubstituted and any combinations thereof;

and wherein any of $R^1$, $R^2$, $R^3$, $R^4$, $R^5$, $R^6$, $R^7$, $R^8$, $R^9$, $R^{11}$, $R^{12}$, $R^{21}$ or $R^{22}$ may further comprise a heteroatom containing side chain wherein said side chain is joined to the R group by a linkage which comprises an ether linkage ($-OR^{25}$), a thioether linkage ($-SR^{25}$), or an amine linkage ($-NR^{25}R^{26}$ or $-N^+R^{25}R^{26}R^{27}$), and wherein $R^{25}$, $R^{26}$ and $R^{27}$ independently comprise hydrogen, Z, an alkyl group wherein said alkyl group is saturated or unsaturated, linear or branched, substituted or unsubstituted, an alkoxy group that is saturated or unsaturated, branched or linear, substituted or unsubstituted, or when taken together, $R^{25}$ and $R^{26}$, and $R^{26}$ and $R^{27}$ independently comprise a five or six membered ring, and wherein any of $R^{25}$, $R^{26}$ or $R^{27}$ may further comprise said heteroatom containing side chain.

In another embodiment of the present invention, the styryl dye comprises a picoline or quinoline moiety instead of a benzazolium group. As such, these dyes have the structure:

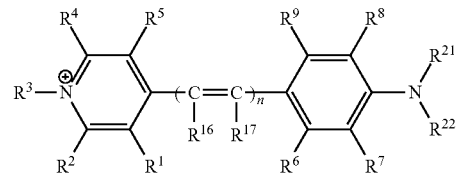

wherein n can be 1, 2 or 3;

wherein at least one of $R^1$, $R^2$, $R^3$, $R^4$, $R^5$, $R^6$, $R^7$, $R^8$, $R^9$, $R^{21}$ or $R^{22}$ comprises Q wherein Q comprises a sulfonate ($SO_3^-$), a sulfonate ester ($SO_2ER^{13}$), a sulfoxide ($SOR^{13}$), a sulfone ($SO_2CR^{13}R^{14}R^{15}$), a sulfonamide ($SO_2NR^{13}R^{14}$), a phosphate ($PO_4^=$), a phosphate monoester ($PO_3^-ER^{13}$), a phosphate diester ($PO_2ER^{13}ER^{14}$), a phosphonate ($PO_3^=$) a phosphonate monoester ($PO_2^-ER^{13}$) a phosphonate diester ($POER^{13}ER^{14}$), a thiophosphate ($PSO_3^=$), a thiophosphate monoester ($PSO_2^-ER^{13}$) a thiophosphate diester ($PSOER^{13}ER^{14}$), a thiophosphonate ($PSO_2^=$), a thiophosphonate monoester ($PSO^-ER^{13}$) a thiophosphonate diester ($PSER^{13}ER^{14}$), a phosphonamide ($PONR^{13}R^{14}NR^{19}R^{20}$), its thioanalogue ($PSNR^{13}R^{14}NR^{19}R^{20}$), a phosphoramide ($PONR^{13}R^{14}NR^{15}NR^{19}R^{20}$), its thioanalogue ($PSNR^{13}R^{14}NR^{15}NR^{19}R^{20}$), a phosphoramidite ($PO_2R^{19}NR^{13}R^{14}$) or its thioanalogue ($POSR^{19}NR^{13}R^{14}$) where E can be independently O or S;

wherein Q is attached directly, or indirectly through a linker arm comprising carbon, sulfur, oxygen, nitrogen, or any combinations thereof and wherein said linker arm may be saturated or unsaturated, linear or branched, substituted or unsubstituted or any combinations thereof and wherein when Q is a sulfonamide, it does not comprise a terminal reactive group or a linker joining the dye to a target molecule;

wherein $R^{13}$, $R^{14}$, $R^{16}$, $R^{19}$ and $R^{20}$ can be hydrogen, a halogen, an amino group, an alkyl group wherein said alkyl group is saturated or unsaturated, linear or branched, substituted or unsubstituted, an alkoxy group wherein said alkoxy group is saturated or unsaturated, branched or linear, substituted or unsubstituted, or when taken together $R^{13}$ and $R^{14}$ form a five or six membered ring;

wherein $R^{16}$, $R^{17}$ and the remaining $R^1$, $R^2$, $R^3$, $R^4$, $R^5$, $R^6$, $R^7$, $R^8$, $R^9$, $R^{21}$ or $R^{22}$ can independently be hydrogen, Z, an alkyl group wherein said alkyl group is saturated or unsaturated, linear or branched, substituted or unsubstituted, an alkoxy group wherein said alkoxy group is saturated or unsaturated, branched or linear, substituted or unsubstituted, or when taken together, $R^1$ and $R^2$, $R^2$ and $R^3$, $R^3$ and $R^4$, $R^4$ and $R^5$, $R^5$ and $R^{16}$, $R^{16}$ and $R^{17}$, $R^{17}$ and $R^9$, $R^9$ and $R^8$, $R^8$ and $R^{21}$, $R^{21}$ and $R^{22}$, $R^{22}$ and $R^7$, and $R^7$ and $R^6$ may form a 5 or 6 membered ring;

wherein Z comprises a carboxyl group ($CO_2^-$), a carbonate ester ($COER^{13}$), a sulfonate ($SO_3^-$), a sulfonate ester ($SO_2ER^{13}$), a sulfoxide ($SOR^{13}$), a sulfone ($SO_2CR^{13}R^{14}R^{15}$), a sulfonamide ($SO_2NR^{13}R^{14}$), a phosphate ($PO_4^=$), a phosphate monoester ($PO_3^-ER^{13}$), a phosphate diester ($PO_2ER^{13}ER^{14}$), a phosphonate ($PO_3^=$) a phosphonate monoester ($PO_2^-ER^{13}$) a phosphonate diester ($POER^{13}ER^{14}$), a thiophosphate ($PSO_3^=$), a thiophosphate monoester ($PSO_2^-ER^{13}$) a thiophosphate diester ($PSOER^{13}ER^{14}$), a thiophosphonate ($PSO_2^=$), a thiophosphonate monoester ($PSO^-ER^{13}$) a thiophosphonate diester ($PSER^{13}ER^{14}$), a phosphonamide ($PONR^{13}R^{14}NR^{19}R^{20}$), its thioanalogue ($PSNR^{13}R^{14}NR^{19}R^{20}$), a phosphoramide ($PONR^{13}R^{14}NR^{15}NR^{19}R^{20}$), its thioanalogue ($PSNR^{13}R^{14}NR^{15}NR^{19}R^{20}$), a phosphoramidite ($PO_2R^{19}NR^{13}R^{14}$) or its thioanalogue ($POSR^{19}NR^{13}R^{14}$) where E can be independently O or S;

where Z is attached directly, or indirectly through a linker arm comprising carbon, sulfur, oxygen, nitrogen, and any combinations thereof and wherein said linker arm may be saturated or unsaturated, linear or branched, substituted or unsubstituted and any combinations thereof;

and wherein any of $R^1$, $R^2$, $R^3$, $R^4$, $R^5$, $R^6$, $R^7$, $R^8$, $R^9$, $R^{21}$ or $R^{22}$ may further comprise a heteroatom containing side chain wherein said side chain is joined to the R group by a linkage which comprises an ether linkage (—$OR^{25}$), a thioether linkage (—$SR^{25}$), or an amine linkage (—$NR^{25}R^{26}$ or —$N^+R^{25}R^{26}R^{27}$), and wherein $R^{25}$, $R^{26}$ and $R^{27}$ independently comprise hydrogen, Z, an alkyl group wherein said alkyl group is saturated or unsaturated, linear or branched, substituted or unsubstituted, an alkoxy group that is saturated or unsaturated, branched or linear, substituted or unsubstituted, or when taken together, $R^{25}$ and $R^{26}$, and $R^{26}$ and $R^{27}$ independently comprise a five or six membered ring, and wherein any of $R^{25}$, $R^{26}$ or $R^{27}$ may further comprise said heteroatom containing side chain.

When $R^4$ and $R^5$ comprise alkyl chains that are joined together, a quinoline moiety can be formed, the dye thereby having the general structure:

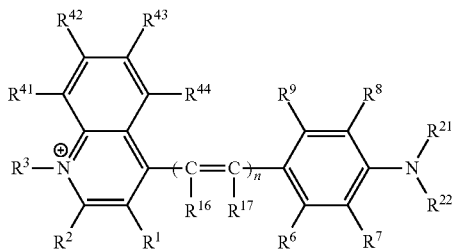

where $R^{41}$, $R^{42}$, $R^{43}$ and $R^{44}$ are as described previously for $R^1$, $R^2$, $R^3$, $R^4$, $R^5$, $R^6$, $R^7$, $R^8$, $R^9$, $R^{21}$ and $R^{22}$.

In another aspect of the present invention, novel dyes that are based upon cyanine dyes are disclosed. In one embodiment the dyes have the general structure:

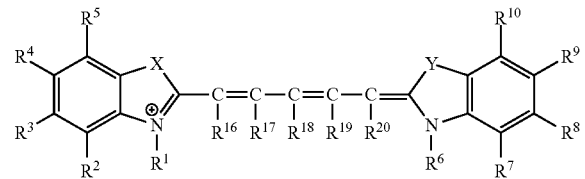

wherein X and Y independently comprise $CR^{11}R^{12}$, $NR^{11}$, O, S or Se, wherein $R^{11}$ and $R^{12}$ independently comprise hydrogen, a halogen, an amino group, an alkyl group wherein said alkyl group is saturated or unsaturated, linear or branched, substituted or unsubstituted, an alkoxy group wherein said alkoxy group is saturated or unsaturated, branched or linear, substituted or unsubstituted, or when taken together, $R^{11}$ and $R^{12}$ comprise a 5 or 6 membered ring;

wherein at least one of $R^1$, $R^2$, $R^3$, $R^4$, $R^5$, $R^6$, $R^7$, $R^8$, $R^9$, $R^{10}$, $R^{11}$, or $R^{12}$ comprises Q, wherein Q comprises a sulfoxide ($SOR^{13}$), a sulfone ($SO_2CR^{13}R^{14}R^{15}$), a sulfonamide ($SO_2NR^{13}R^{14}$), a phosphate monoester ($PO_3^-ER^{13}$), a phosphate diester ($PO_2ER^{13}ER^{14}$), a phosphonate monoester ($PO_2^-ER^{13}$), a phosphonate diester ($POER^{13}ER^{14}$), a thiophosphate ($PSO_3^=$), a thiophosphate monoester ($PSO_2^-ER^{13}$), a thiophosphate diester ($PSOER^{13}ER^{14}$), a thiophosphonate ($PSO_2^=$), a thiophosphonate monoester ($PSO^-ER^{13}$), a thiophosphonate diester ($PSER^{13}ER^{14}$), a phosphonamide ($PONR^{13}R^{14}NR^{21}R^{22}$), its thioanalogue ($PSNR^{13}R^{14}NR^{21}R^{22}$), a phosphoramide ($PONR^{13}R^{14}NR^{15}NR^{21}R^{22}$), its thioanalogue ($PSNR^{13}R^{14}NR^{15}NR^{21}R^{22}$), a phosphoramidite ($PO_2R^{21}NR^{13}R^{14}$), or its thioanalogue ($POSR^{21}NR^{13}R^{14}$), wherein any of E independently comprises O or S and the structures are as described previously;

wherein Q is attached directly, or indirectly through a linker arm comprising carbon, sulfur, oxygen, nitrogen, and any combinations thereof and wherein said linker arm may be saturated or unsaturated, linear or branched, substituted or unsubstituted and any combinations thereof and wherein when Q is a sulfonamide, Q does not have a terminal reactive group or a linker arm joining the dye to a target molecule;

wherein $R^{13}$, $R^{14}$, $R^{15}$, $R^{21}$, $R^{22}$ and the remaining $R^1$, $R^2$, $R^3$, $R^4$, $R^5$, $R^6$, $R^7$, $R^8$, $R^9$, $R^{10}$, $R^{11}$, and $R^{12}$, independently comprise hydrogen, Z, a halogen, an amino group, an alkyl group wherein said alkyl group is saturated or unsaturated, linear or branched, substituted or unsubstituted, an alkoxy group wherein said alkoxy group is saturated or unsaturated, branched or linear, substituted or unsubstituted, or when taken together $R^2$ and $R^3$, $R^3$ and $R^4$, $R^4$ and $R^5$, $R^7$ and $R^8$, $R^8$ and $R^9$, $R^9$ and $R^{10}$, $R^1$ and $R^{16}$, $R^6$ and $R^{20}$ independently comprise a five or six membered ring;

$R^{16}$, $R^{17}$, $R^{18}$, $R^{19}$ and $R^{20}$ independently comprise hydrogen, Z, a halogen, an amino group, an alkyl group wherein said alkyl group is saturated or unsaturated, linear or branched, substituted or unsubstituted, an alkoxy group wherein said alkoxy group is saturated or unsaturated, branched or linear, substituted or unsubstituted, or when taken together $R^{17}$, $R^{18}$ and $R^{19}$ can form substituted or unsubstituted five or six membered ring;

wherein Z is attached directly or indirectly through a linker arm comprising carbon, sulfur, oxygen, nitrogen, and any combinations thereof and wherein said linker arm is saturated or unsaturated, linear or branched, substituted or unsubstituted, or any combinations thereof;

and wherein any of $R^1$, $R^2$, $R^3$, $R^4$, $R^5$, $R^6$, $R^7$, $R^8$, $R^9$, $R^{10}$, $R^{11}$ or $R^{12}$ may further comprise a heteroatom containing side chain, wherein said side chain is joined to the R group by a linkage which comprises an ether linkage (—$OR^{25}$), a thioether linkage (—$SR^{25}$), or an amine linkage (—$NR^{25}R^{26}$ or —$N^+R^{25}R^{26}R^{27}$), and wherein $R^{25}$, $R^{26}$ and $R^{27}$ independently comprise hydrogen, Z, a halogen, an amino group, an alkyl group wherein said alkyl group is saturated or unsaturated, linear or branched, substituted or unsubstituted, an alkoxy group wherein said alkoxy group is saturated or unsaturated, branched or linear, substituted or unsubstituted, or when taken together $R^{25}$ and $R^{26}$ and $R^{26}$ and $R^{27}$ independently comprise a five or six membered ring, and wherein any of $R^{25}$, $R^{26}$ or $R^{27}$ may further comprise said heteroatom containing side chain.

Complex Ring Structures

As described above some of the R groups may be joined together to form one or more fused 5 or 6 membered ring structures. It is understood that the complex rings that are formed by closure of R groups may be further substituted with any of the R groups described previously. Examples of complex rings that may be formed for the benzazolium portion of cyanine and asymmetric cyanine dyes can comprise but not be limited to:

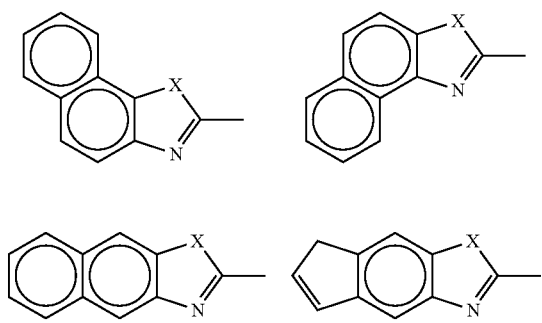

In addition, "rigid" cyanine dyes have been described wherein a fused ring is formed where the nitrogen of the benzazolium is linked to the nearest carbon of the methine bridge (U.S. Pat. No. 6,133,445 and U.S. Pat. No. 6,686,145 both of which are hereby incorporated by reference). Similarly in a cyanine dye with a monomethine bridge (i.e. when n=0), a rigid linkage can be formed by joining the nitrogens of the benzazolium group to each other (U.S. Pat. No. 5,852,191 and U.S. Pat. No. 5,981,747 both of which are incorporated by reference).

If desired, a variation of the preceding dyes can be the substitution of an azabenzazolium instead of a benzazolium moiety in the cyanine, asymmetric cyanine and styrene dyes; i.e. a Nitrogen replaces the carbon in the positions where $R^2$, $R^3$, $R^4$, $R^5$, $R^7$, $R^8$, $R^9$ or $R^{10}$ are connected to the benzazolium moiety of cyanine dyes or to the $R^2$, $R^3$, $R^4$ or $R^5$ positions of the asymmetric cyanine and styrene dyes disclosed previously. Methods for the synthesis and use of an azabenzazolium based dyes are disclosed in U.S. Pat. No. 6,664,047 B1, hereby incorporated by reference. As such these moieties would have the structures:

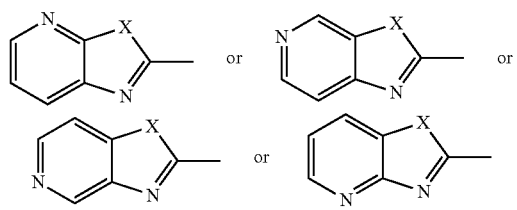

Examples of rings and complex rings that may comprise the non-benzazolium portion of an asymmetric cyanine dye can comprise but not be limited to:

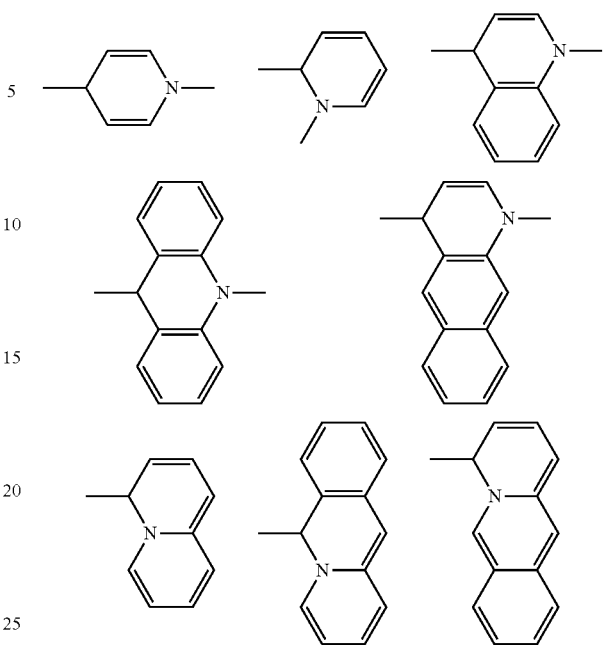

Examples of rings and complex rings that may be part of the non-benzazolium portion of a styryl dye can comprise but not be limited to:

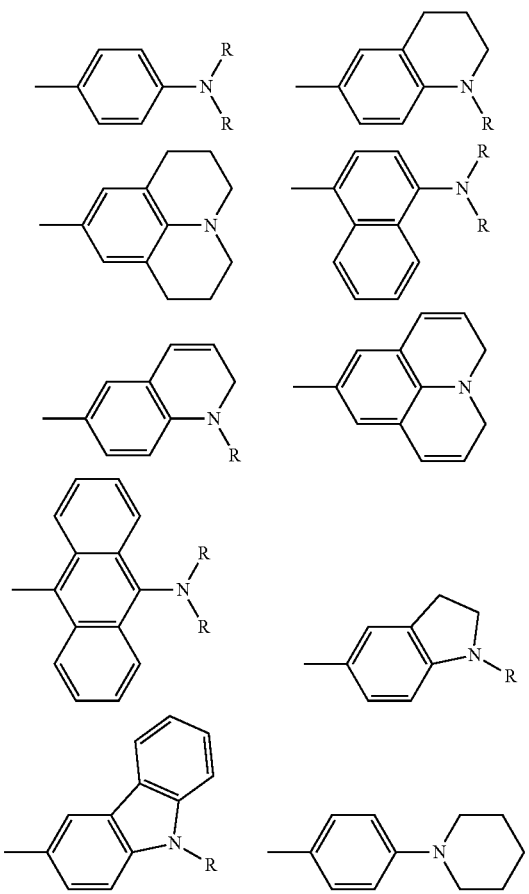

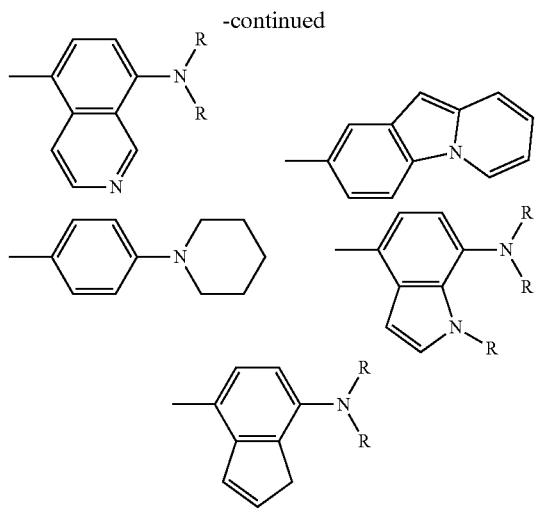

Reactive Groups and Targets

In another aspect of the present invention, one of the R groups is a reactive group thereby allowing the dyes of the present invention to be attached to a useful target molecule. Examples of reactive groups that may find use in the present invention can include but not be limited to a nucleophilic reactive group, an electrophilic reactive group, a terminal alkene, a terminal alkyne, a platinum coordinate group or an alkylating agent.

There are a number of different electrophilic reactive groups that may find use with the present invention; examples can include but not be limited to isocyanate, isothiocyanate, monochlorotriazine, dichlorotriazine, 4,6,-dichloro-1,3,5-triazines, mono- or di-halogen substituted pyridine, mono- or di-halogen substituted diazine, maleimide, haloacetamide, aziridine, sulfonyl halide, acid halide, hydroxysuccinimide ester, hydroxysulfosuccinimide ester, imido ester, hydrazine, azidonitrophenol, azide, 3-(2-pyridyl dithio)-propionamide, glyoxal and aldehyde groups. Nucleophilic reactive groups can include but not be limited to reactive thiol, amine and hydroxyl groups. For purposes of synthesis of dyes, reactive thiol, amine or hydroxyl groups can be protected during various synthetic steps and the reactive groups generated after removal of the protective group. Use of a terminal alkene or alkyne groups for attachment of markers has been previously described in U.S. Patent Application Serial No. 2003/0225247, hereby incorporated by reference. The use of platinum coordinate groups for attachment of other dyes has been previously disclosed in U.S. Pat. No. 5,580,990 and the use of alkyl groups has been previously described in U.S. Pat. No. 6,593,465 B1, both of which patents are hereby incorporated by reference.

Examples of useful target molecules can include but not be limited to a nucleoside, nucleotide, oligonucleotide, polynucleotide, peptide nucleic acid, protein, peptide, enzyme, antigen, antibody, hormone, hormone receptor, cellular receptor, lymphokine, cytokine, hapten, lectin, avidin, strepavidin, digoxygenin, carbohydrate, oligosaccharide, polysaccharide, lipid, liposomes, glycolipid, viral particle, viral component, bacterial cell, bacterial component, eucaryotic cell, eukaryotic cell component, natural drug, synthetic drug, glass particle, glass surface, natural polymers, synthetic polymers, plastic particle, plastic surface, silicaceous particle, silicaceous surface, organic molecule, dyes and derivatives thereof.

The nucleoside, nucleotide, oligonucleotide, or polynucleotide can comprise one or more ribonucleoside moieties, ribonucleotide moieties, deoxyribonucleoside moieties, deoxyribonucleotide moieties, modified ribonucleosides, modified ribonucleotides, modified deoxyribonucleosides, modified deoxyribonucleotides, ribonucleotide analogues, deoxyribonucleotide analogues and any combination thereof.

As described above, the dyes of the present invention may have dyes as targets thereby creating composite dyes. By joining the dyes of the present invention to another dye, unique properties may be enjoyed that are not present in either dye alone. For instance, if one of the dyes of the present invention is joined to another dye such that it creates an extended conjugation system, the spectral characteristics of the dye may be different than either dye component. Another example of this method is where the conjugation systems do not overlap but the proximity allows an internal energy transfer to take place thereby extending the Stokes shift. For an example of this, see U.S. Pat. No. 5,401,847, U.S. Pat. No. 6,008,373 B1 and U.S. Pat. No. 5,800,996, all three of which patents are hereby incorporated by reference. Other properties may also be enhance by this joining, for example, it has been previously described that the joining together of two ethidium bromide molecules generates a dye that has enhanced binding to nucleic acids (U.S. Patent Application Publication No. 2003/0225247, hereby incorporated by reference). Other composite dyes have been described that simultaneously enjoy both properties, i.e. enhanced binding and energy transfer (U.S. Pat. No. 5,646,264, hereby incorporated by reference). Furthermore, these composites dyes are not limited to binary constructs of only two dyes, but may comprise oligomeric or polymeric dyes. These composite dyes may be comprised of the same dye or different dyes may be joined together depending upon the properties desired.

Utility may also be achieved by attaching a dye of the present invention to a target specific moiety. Thus, binding between the target specific moiety and its corresponding target may be monitored by essentially determining the presence or amount of dye that is bound to the target. Well-known examples of such assays are hybridizations between complementary nucleic acids as well as binding that take place between antibodies and their corresponding antigens. Other binding pairs that may be of interest can include but not be limited to ligand/receptor, hormone/hormone receptor, carbohydrate/lectin and enzyme/substrate. Assays may be carried out where one component is fixed to a solid support and a corresponding partner is in solution. By binding to the component fixed to the support, the partner now becomes attached to the support as well. A well-known example of this method is the microarray assays where labeled analytes become bound to discrete sites on the microarray. Homogeneous probe dependent assays are also well known in the art and may take advantage of the present invention. Examples of such methods are energy transfer between adjacent probes (U.S. Pat. No. 4,868,103), the Taqman exonuclease assay (U.S. Pat. No. 5,538,848 and U.S. Pat. No. 5,210,015), Molecular Beacons (U.S. Pat. No. 5,118,801 and U.S. Pat. No. 5,925,517) and various real time assays (U.S. patent application Ser. No. 10/096,076), all of which are incorporated by reference.

Antibodies labeled with dyes of the present invention may be used in various formats. For example, an antibody with one of the dyes of the present invention may be used in an immunofluorescent plate assay or in situ analysis of the cellular location and quantity of various antigenic targets. Antibodies labeled with dyes may also be used free in solution in cell counting or cell sorting methods that use a flow cytometer or for in-vitro and in-vivo imaging of animal models.

The presence or absence of a signal may then be used to indicate the presence or absence of the target itself. An example of this is a test where it is sufficient to know whether a particular pathogen is present in a clinical specimen. On the other hand, quantitative assays may also be carried out where it is not so much the intention of evaluating if a target is present but rather the particular amount of target that is present. An example of this is the previously cited microarray assay where the particular rise or fall in the amount of particular mRNA species may be of interest.

In another embodiment of the present invention, dyes that have been disclosed above as well as dyes described previous literature may be attached to a carrier with a more general affinity. Dyes may be attached to intercalators that in themselves do not provide signal generation but by virtue of their binding may bring a dye in proximity to a nucleic acid. A further example is attachment of dyes to SDS molecules thereby allowing dyes to be brought into proximity to proteins. Thus this embodiment describes the adaptation of a dye or dyes that lack affinity to a general class of molecules may be adapted by linking them to non-dye molecules or macromolecules that can convey such properties.

Various applications may enjoy the benefits of binding the dyes of the present invention to appropriate targets. As described above, staining of macromolecules in a gel is a methodology that has a long history of use. More recent applications that also may find use are real time detection of amplification (U.S. Pat. No. 5,994,056, U.S. Pat. No. 6,174,670 and U.S. patent application Ser. No. 10/096,076, all of which are hereby incorporated by reference), and binding of nucleic acids to microarrays. In situ assays may also find use where the binding of dyes of the present invention is used to identify the location or quantity of appropriate targets.

Selected embodiments of the compounds of this invention include but are not limited to following:

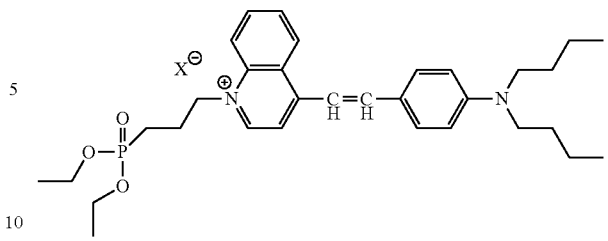

wherein X comprises an anion.

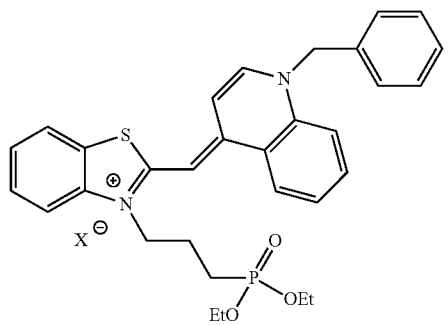

wherein X comprises an anion.

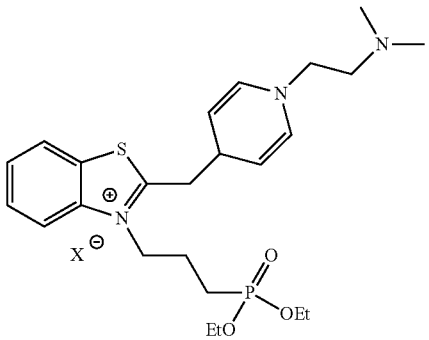

wherein X comprises an anion.

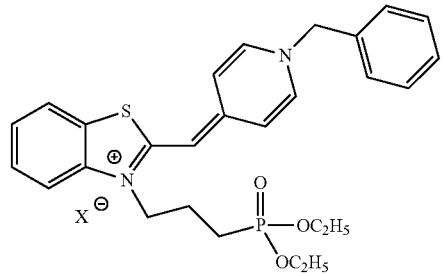

wherein X comprises an anion.

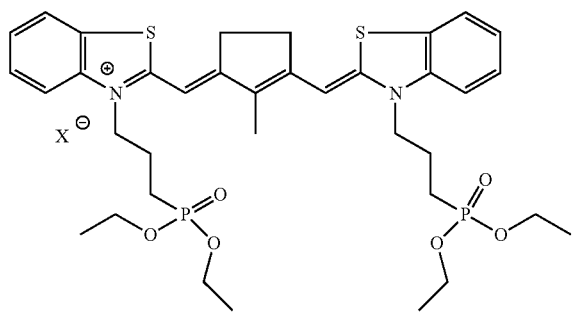

wherein X comprises an anion.

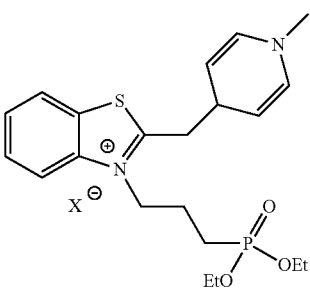

wherein X comprises an anion.

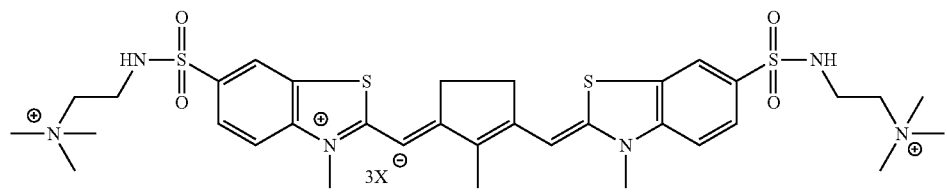
wherein X comprises an anion.
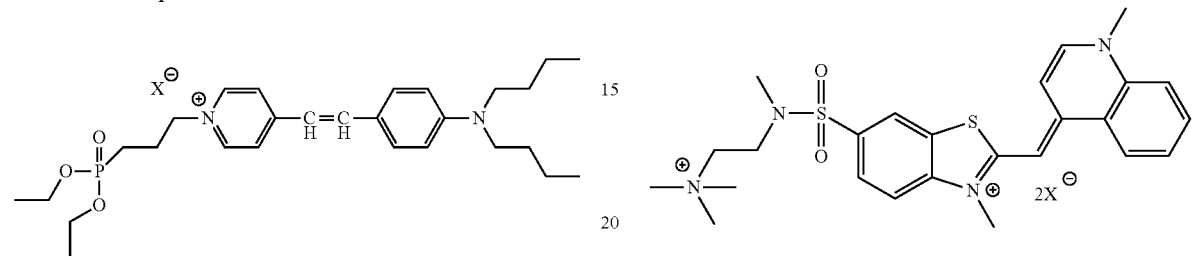
wherein X comprises an anion.
wherein X comprises an anion.
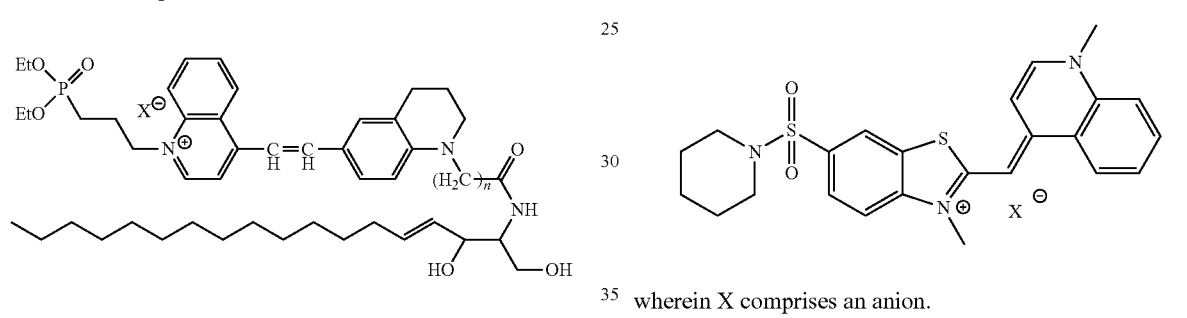
wherein X comprises an anion.
wherein X comprises an anion.
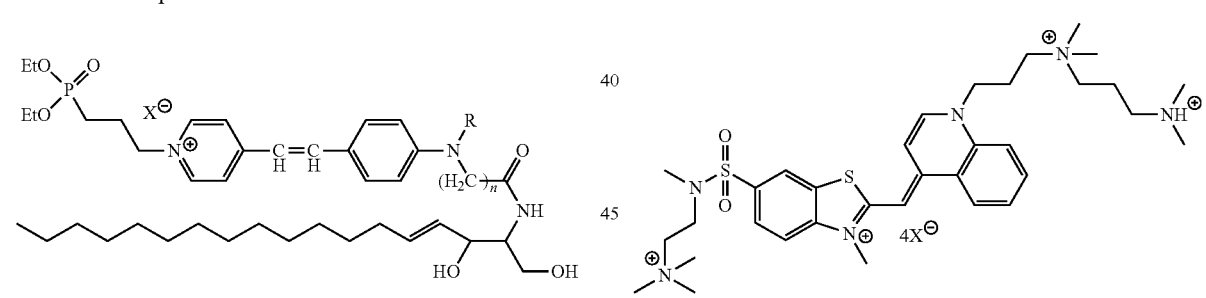
wherein X comprises an anion.
wherein X comprises an anion.
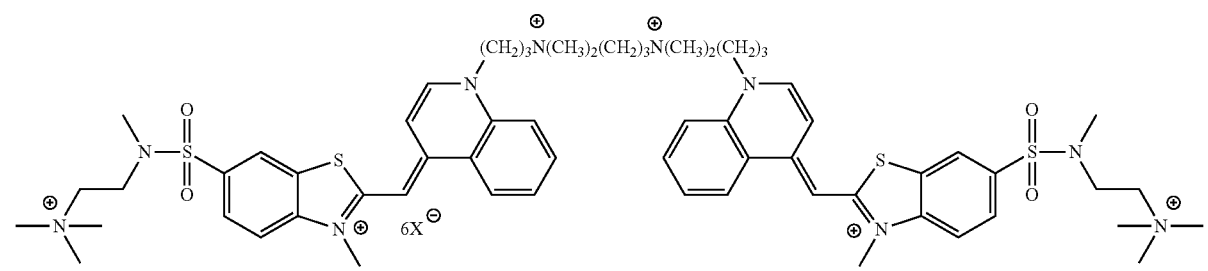
wherein X comprises an anion.

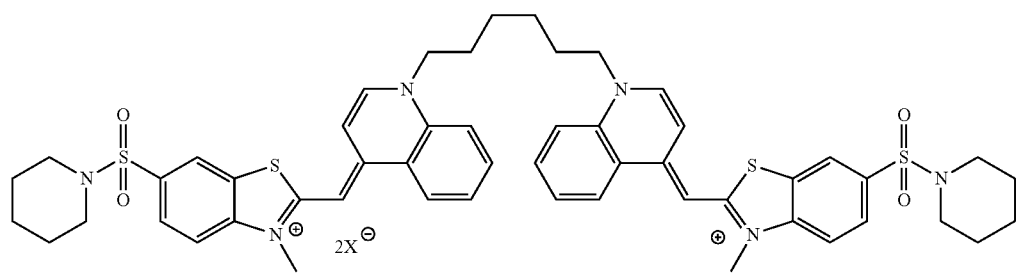

wherein X comprises an anion.

As described above, the anions described above serve as counterions for the compounds and dyes of the present invention. Examples of cations that may serve as counterions include but are not be limited to hydrogen, sodium, potassium, lithium, calcium, cesium, ammonium, alkyl ammonium, alkoxy ammonium and pyridinium. When a dye comprises a cationic group, an anionic counterion will also be present. Any anion may serve this purpose as long as it doesn't interfere with the use of the dye. Examples of anions that may serve as counterions include but are not limited to halides such as a bromide, chloride, fluoride and iodide. Other examples of anions that can serve as counterions include but are not limited to perchlorate ($ClO_4^-$), sulfate ($SO_4^=$), sulfonate, alkane sulfonate, aryl sulfonate, phosphate, tosylate, mesylate and tetrafluoroborate moieties.

As also described above, in some cases the counterion or counterions are provided by the dye being presented as a salt where it exists as separate ionic species. In other cases, the counterion or counterions may be present as part of the compound (sometimes called inner salts). It is understood that a combination of ions may be provided by the compound and salts. With regard to acid moieties that are shown in forms such as COOH, it should be understood and appreciated that these compounds may be found in ionized forms such as $COO^-$. It should also be appreciated by those skilled in the art that the stoichiometric number of counterion or counterions which balance the charge or charges on the compounds of the present invention can be the same or they can be different, provided that the counterions balance the charge(s) on the compound. The combination of counterions can be selected from any of the anions described above. Similarly, the combination of counterions can also be selected from any of the cations described above.

The examples which follow are set forth to illustrate various aspects of the present invention but are not intended in any way to limit its scope as more particularly set forth and defined in the claims that follow thereafter.

DESCRIPTION OF THE PREFERRED EMBODIMENTS

Example 1

Synthesis of Dye 1

(a) Preparation of 1-benzyl-4-methylpyridinium bromide (Compound 1)

To a solution of 4-picoline (9.3 g, 0.1 mol) in toluene (200 mL), benzyl bromide (34.2 g, 0.2 mol) was added dropwise at room temperature. After the addition, the mixture was heated to reflux for 5 hrs. The mixture was cooled to room temperature. The precipitate formed was collected by filtration, washed with toluene and dried under vacuum to give Compound 1 as white solid (21.4 g, 81%). It was used without further purification. The structure of Compound 1 is given below:

Compound 1

(b) Preparation of 3-(3-(diethoxyphosphoryl)propyl)-2-(methylthio)benzo[d]thiazole-3-ium bromide (Compound 2)

A mixture of 2-methylthiobenzothiazole (2.4 g, 13.2 mmol) and diethyl (3-bromopropyl)phosphonate (4.18 g, 16.1 mmol) was heated at 150° C. for 5 hrs. After the mixture was cooled to room temperature, ethyl acetate was added. The precipitate formed was collected by centrifugation, washed with ethyl acetate and dried under vacuum. The crude Compound 2 (1.24 g, 21%) was used without further purification. The structure of Compound 2 is given below:

Compound 2

(c) Preparation of Dye 1

Triethylamine (75 mg, 0.75 mmol) was added to a mixture of Compound 1 (0.19 g, 0.75 mmol) and Compound 2 (0.33 g, 0.75 mmol) in dichloromethane (10 mL). The mixture was stirred at room temperature for 5 hrs. The solvent was removed under vacuum. The residue was purified by flash chromatography to provide Dye 1 (90.5 mg, 21%). Abs (max, methanol)=450 nm; Em (water)=476 nm. The structure of Dye 1 is given below:

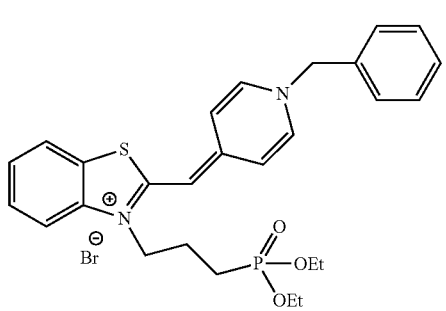

Dye 1

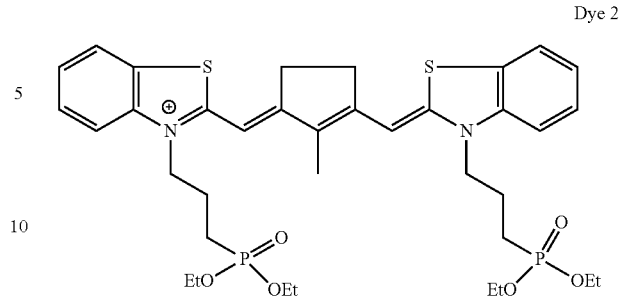

Dye 2

Example 2

Synthesis of Dye 2

(a) Preparation of 3-(3-(diethoxyphosphoryl)propyl)-2-methylbenzo[d]thiazole-3-ium bromide (Compound 3)

A mixture of 2-methybenzothiazole (0.36 g, 2.4 mmol) and diethyl (3-bromopropyl)phosphonate (0.67 g, 2.6 mmol) was heated at 130° C. for 4 hrs. After the mixture was cooled to room temperature, ethyl acetate was added. The precipitate formed was collected by centrifugation, washed with ethyl acetate and dried under vacuum to provide Compound 3 (0.37 g). This product was used without further purification. The structure of Compound 3 is given below:

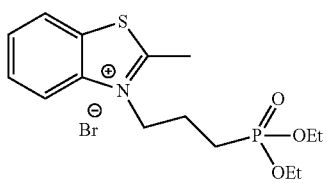

Compound 3

(b) Preparation of Dye 2

A mixture of Compound 3 (0.2 g, 0.49 mmol) and 2-methylcyclopentane-1,3-dione (0.045 g, 0.4 mmol) was heated in a pressure tube at 210° C. for 2 hrs. After the mixture was cooled to room temperature, the melt was dissolved in warm DMF (2 mL) and then slowly added to vigorously stirred ethyl acetate (20 mL). Precipitated dye was collected by centrifugation, washed with ethyl acetate and dried. Crude dye was purified on Biotage (Si 25+M) using a gradient of methanol in chloroform to provide Dye 2 as a dark green solid (0.12 g). Abs (max, methanol)=610 nm. The structure of Dye 2 is given below:

Example 3

Synthesis of Dye 3

(a) Preparation of Ethyl 3-(4-methylquinolinium-1-yl) propylphosphonate (Compound 4)

A mixture of lepidine (1.0 g, 7.0 mmol) and diethyl(3-bromopropyl)-phosphonate (2.0 g, 7.7 mmol) was heated in a pressure tube at 130° C. for 4 hours. The mixture was allowed to cool to room temperature, and the resulting mass was dissolved in DMF (4 ml). The combined mixture was then added dropwise to ethyl acetate (40 ml). An oily residue was obtained which was washed with ethyl acetate (2×40 ml) and dried under vacuum to yield 1.9 g of Compound 4 which was then used without any further purification. The structure of Compound 4 is given below:

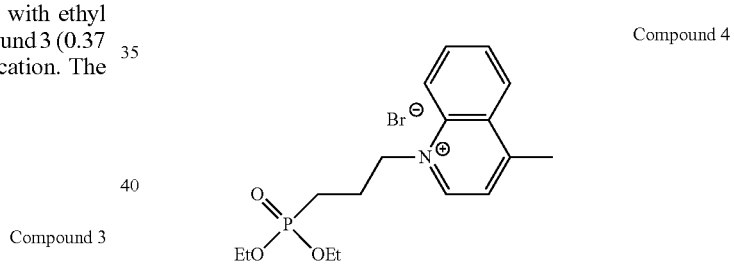

Compound 4

(b) Preparation of Dye 3

A mixture of Compound 4 (0.67 g, 1.66 mmol), 4-(dibutylamino)-benzaldehyde (0.43 g, 1.83 mmol) and piperidine (72 μL, 0.73 mmol) was refluxed in ethanol (5 ml) for 18 hours. The reaction mixture was cooled to room temperature and ethanol was evaporated and the residue thus obtained was purified by flash chromatography using 10% methanol in chloroform to yield 0.14 g of Dye 3. Abs (max, methanol) =540 nm; Em=640 nm. The structure of Dye 3 is given below:

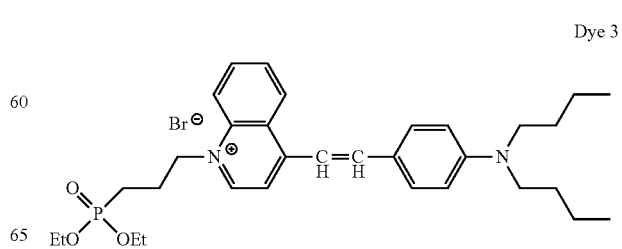

Dye 3

Example 4

Synthesis of Dye 4

(a) Preparation of 1-benzyl-4-methylquinolinium bromide (Compound 5)

To a solution of lepidine (14.3 g, 0.1 mol) in toluene (200 mL), benzyl bromide (34.2 g, 0.2 mol) was added dropwise at room temperature. After the addition, the mixture was heated to reflux for 5 hrs. The mixture was cooled to room temperature; the precipitate formed was collected by filtration, washed with toluene and dried under vacuum to give Compound 5 as yellow solid (18.2 g, 58%). It was used without further purification. The structure of Compound 5 is given below:

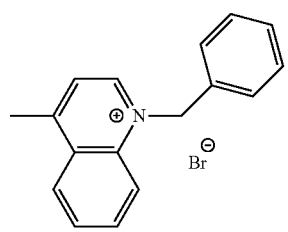

Compound 5

(b) Preparation of Dye 4

Triethylamine (0.14 g, 1.4 mmol) was added to a mixture of Compound 2 (0.62 g, 1.4 mmol) (from step (b) of Example 1) and Compound 5 (0.44 g, 1.4 mmol) in dichloromethane (20 mL). The mixture was stirred at room temperature for 5 hrs. The solvent was removed under vacuum. The residue was purified by liquid chromatography to provide Dye 4 as a solid (0.116 g, 13%).

Abs (max, methanol, 50 mM)=507 nm; Em (PBS, 1 µM)=527 nm. The structure of Dye 4 is given below:

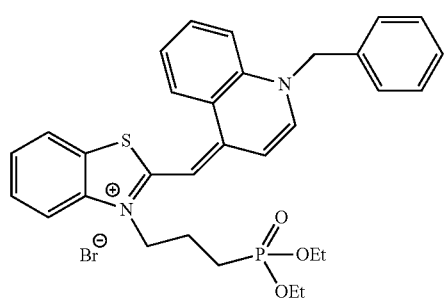

Dye 4

Example 5

Synthesis of Dye 5

(a) Preparation of 1-(2-dimethylamino)ethyl)-4-methylpyridinium bromide (Compound 6)

A mixture of lepidine (3.4 g, 36 mmol) and bromoethyl-dimethylamine (4.6 g, 30 mmol) in toluene (40 mL) was heated to reflux for 6 hrs. The mixture was cooled to room temperature. The precipitate formed was collected by filtration, washed with toluene and dried under vacuum to give Compound 6 as yellow solid (3.1 g, 42%). It was used without further purification. The structure of Compound 6 is given below:

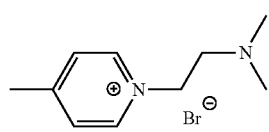

Compound 6

(b) Preparation of Dye 5

To a mixture of Compound 2 (176 mg, 0.40 mmol) (from step (b) of Example 1) and Compound 6 (123 mg, 0.50 mmol) in dichloromethane (10 mL), triethylamine (50 mg, 0.50 mmol) was added. The mixture was stirred at room temperature overnight. The solvent was removed under vacuum. The residue was purified by liquid chromatography to provide Dye 5 (17.3 mg, 7.8%). Abs (max, methanol, 50 mM)=422 nm; Em (methanol)=472 nm. The structure of Dye 5 is given below:

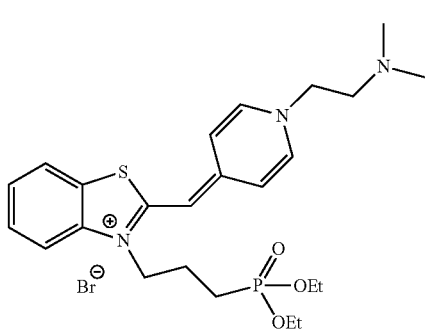

Dye 5

Example 6

Synthesis of Dye 6

(a) Preparation of 1,4-dimethylpyridinium iodide (Compound 7)

To a solution of 4-picoline (18.6 g, 0.2 mol) in toluene (100 mL), methyl iodide (56.8 g, 0.4 mol) was added dropwise at room temperature. After the addition, the mixture was stirred at room temperature for 5 hrs. The precipitate was collected by filtration, washed with toluene and dried under vacuum to give Compound 7 as an off-white solid (31.6 g, 67%). The structure of Compound 7 is given below:

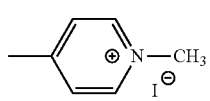

Compound 7

(b) Preparation of Dye 6

To a mixture of Compound 2 (0.22 g, 0.50 mmol) (from step (b) of Example 1) and Compound 7 (0.12 g, 0.50 mmol) in dichloromethane (10 mL), triethylamine (50 mg, 0.50 mmol) was added. The mixture was stirred at room temperature for 5 hrs. The solvent was removed under vacuum. The residue was purified by liquid chromatography to provide Dye 6 as a solid (25 mg, 10%). Abs (max, methanol)=423 nm; Em (methanol)=472 nm. The structure of Dye 6 is given below:

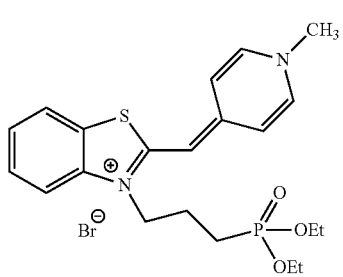

Dye 6

Example 7

Synthesis of Dye 7

(a) Preparation of 2-methylbenzothiazole-6-sulfonyl chloride (Compound 8)

Chlorosulfonic acid (20 ml, 335.0 mmol) was cooled in an ice bath and 2-methylbenzothiazole (10.0 g, 67.0 mmol) was carefully added dropwise over a period of 30 minutes. The combined mixture was heated at 115-120° C. for 15 hours and after cooling, the mixture was added very slowly to ca. 200 ml ice/water mix. A sticky white solid separated which was extracted into chloroform (300 ml). The organic layer was washed with water (2×, 350 ml), washed with brine (2×, 350 ml), dried and evaporated to yield 11.2 g (67%) of a colorless oil (Compound 8) which solidified upon cooling, $R_f$=0.5 (30% ethyl acetate in hexane). The structure of Compound 8 is given below:

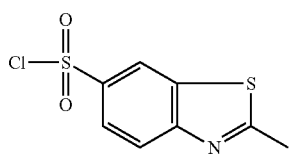

Compound 8

(b) Preparation of N-(2-(dimethylamino)ethyl)-2-methylbenzo[d]thiazole-6 sulfonamide (Compound 9)

To a solution of Compound 8 (7.0 g, 28.26 mmol) in THF (70 mL), a mixture of triethylamine (7.9 mL, 56.52 mmol) and N,N-dimethylethylene-diamine (4.67 mL, 42.38 mmol) in 20 mL THF was added dropwise. The combined mixture was stirred at room temperature for 2 hours during which time TLC showed complete disappearance of Compound 8. Solvents were removed in the rotary evaporator and the residue thus obtained was partitioned between chloroform (100 mL) and water (100 mL). The organic layer was washed with water (2×100 mL), brine (1×100 mL), dried (sodium sulfate) and evaporated to provide Compound 9 as a sticky oily solid (7.1 g, 84% yield). It was used further in the synthesis without any purification. The structure of Compound 9 is given below:

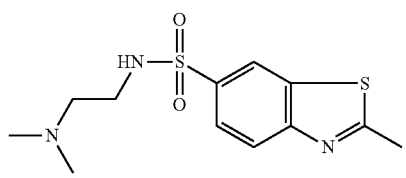

Compound 9

(c) Preparation of 2,3-dimethyl-6-(N-(2-(trimethylammonio)ethyl)sulfamoyl)benzo[d]thiazole-3-ium ditosylate (Compound 10)

To a solution of compound 9 (7.0 g, 23.4 mmol) in acetonitrile (40 mL), methyl p-toluene sulfonate (14 mL, 93.5 mmol) was added. The combined mixture was refluxed for 18 hours and after cooling was added to 350 mL ethyl acetate. A sticky solid was obtained. Solvents were decanted and more ethyl acetate was added to the sticky residue and it was vigorously stirred. This process was repeated until a free-flowing solid was obtained. The solid was then collected by centrifugation, washed with ethyl acetate and dried under vacuum to yield 15.03 g of Compound 10, whose structure is given below:

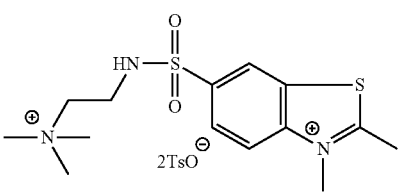

Compound 10

(d) Preparation of Dye 7

A mixture of compound 10 (0.5 g, 0.74 mmol) and 2-methylcyclopentane-1,3-dione (0.085 g, 0.74 mmol) was heated in a pressure tube at 210° C. for 2 hrs. After the mixture was cooled to room temperature, the melt was dissolved in warm DMF (2 mL) and then slowly added to vigorously stirred ethyl acetate (20 mL). Precipitated dye was collected by centrifugation, washed with ethyl acetate and dried. Crude dye was purified on Biotage (RPSi 25+M) using a gradient of acetonitrile in 0.1% aqueous TFA to provide Dye 7 as a dark green solid (0.3 g). Abs (max, methanol)=616 nm. The structure of Dye 7 is given below:

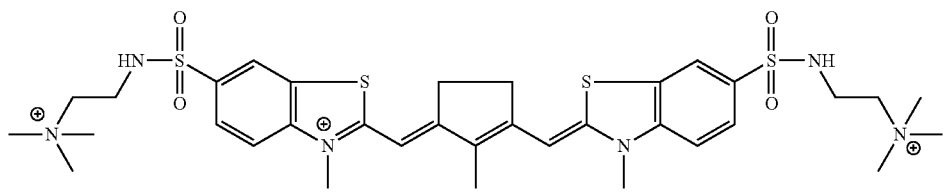

Dye 7

Example 8

Synthesis of Dye 8

(a) Preparation of 1-(3-(diethoxyphosphoryl)propyl)-4-methylpyridinium bromide (Compound 11)

A mixture of picoline (0.5 g, 5.4 mmol) and diethyl(3-bromopropyl)-phosphonate (1.54 g, 5.9 mmol) was heated in a pressure tube at 130° C. for 4 hours. The mixture was allowed to cool to room temperature, and the resulting mass was dissolved in DMF (4 ml). The combined mixture was then added drop wise to ethyl acetate (40 ml). An oily residue was obtained which was washed with ethyl acetate (2×40 ml) and dried under vacuum to yield 1.7 g of Compound 11 which was then used without any further purification. The structure of Compound 11 is given below:

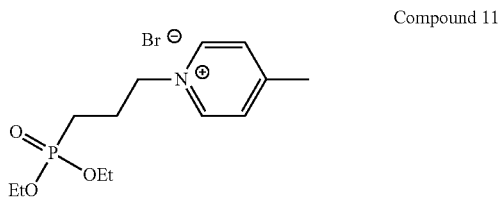 [SMILES: [Br-] ; CCOP(=O)(CCC[n+]1ccc(C)cc1)OCC]

Compound 11

(b) Preparation of Dye 8

A mixture of compound 11 (0.5 g, 1.42 mmol), 4-(dibutylamino)-benzaldehyde (0.37 g, 1.56 mmol) and piperidine (62 µL, 0.63 mmol) was refluxed in ethanol (5 ml) for 18 hours. The reaction mixture was cooled to room temperature and ethanol was evaporated and the residue thus obtained was purified on Biotage (Si 25+M) using a gradient of methanol in chloroform to yield 0.2 g of Dye 8. Abs (max, PBS)=490 nm; Em=610 nm. The structure of Dye 8 is given below:

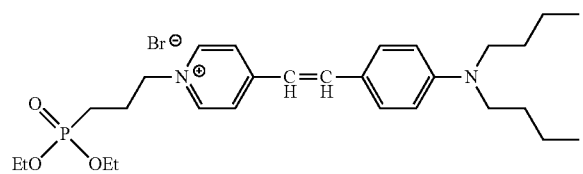

Dye 8

Example 9

Synthesis of Dye 9

(a) Preparation of N-(6-carboxyl hexane)-2,3,4 tetrahydro quinoline (Compound 12)

A mixture of 1,2,3,4-tetrahydroquinoline (10.0 g, 75.0 mmol), 6-bromohexanoic acid (21.9 g, 112.5 mmol) and triethylamine (11.4 g, 112.5 mmol) in 50 ml ethanol was refluxed for 16 hours. The reaction mixture was cooled and precipitated solid was then separated by filtration. The remaining solvents were removed in a rotary evaporator and to the residue thus obtained 200 ml ethyl acetate and 200 ml water was added. The organic layer was separated, washed with water and brine, dried over sodium sulfate and evaporated to dryness to yield 20.0 g of dark brown oil (Compound 12) with the structure given below.

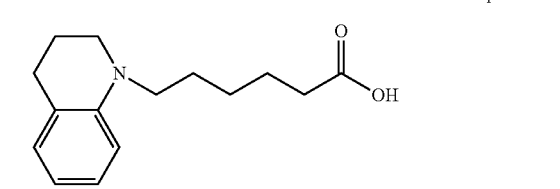

Compound 12

(b) Preparation of N-(6-carboxyl hexane)-2,3,4 tetrahydro-7-formyl quinoline (Compound 13)

POCl$_3$ (1.87 g, 12.2 mmol) was added dropwise to DMF (5 mL) which was cooled in an ice bath. The combined mixture was stirred for 20 minutes and to this a solution of Compound 12 (1.5 g, 6.1 mmol) in DMF (10 mL) was added dropwise. After the addition was complete, the ice bath was removed and the reaction mixture was stirred at room temperature for 1 hour. An aqueous solution of sodium acetate (25% w/w, 10 mL) was then added to the reaction mixture and it was heated in an oil bath (T=110° C.) for 30 min. The reaction mixture was cooled and poured into ca. 500 ml water and extracted with ethyl acetate. The organic layer was washed twice with water followed by brine, dried over sodium sulfate and then evaporated to dryness to yield 1.31 g of a dark brown liquid which was used without any further purification. The structure of Compound 13 is given below:

Compound 13

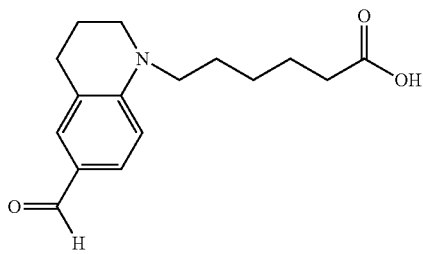

(c) Preparation of Dye 9

A mixture of Compound 4 (0.195 g, 0.48 mmol), Compound 13 (0.2 g, 0.73 mmol) and piperidine (29 μL, 0.29 mmol) was refluxed in ethanol (5 ml) for 16 hours. The reaction mixture was cooled to room temperature, ethanol evaporated and the residue thus obtained was purified on Biotage (Si 25+M) using a gradient of methanol in methylene chloride to yield 84 mg of Dye 9. Abs (max, methanol)=585 nm; Em=690 nm. The structure of Dye 9 is given below:

Dye 9

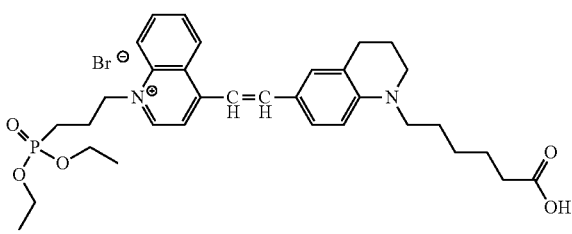

Example 10

Synthesis of Dye 9-Sphingosine conjugate

To a mixture of Dye 9 (32.2 mg, 48.8 μmol), triphenylphosphine (25.6 mg, 97.6 μmol) and 2,2'-dipyridyl disulfide (21.5 mg, 97.6 μmol), a solution of D-sphingosine (17.5 mg, 58.6 μmol) in methylene chloride (1 mL) was added. The combined mixture was stirred at room temperature for 5 hours and the product was purified on Biotage (Si, 12+M) using a gradient of methanol in methylene chloride to yield 25.2 mg of Dye 9-sphingosine conjugate. Abs (max, PBS)=567 nm; Abs (max, methanol)=580 nm; Em (PBS containing 1 mg/mL BSA)=668 nm. The structure of Dye 9-sphingosine conjugate is given below:

Dye 9

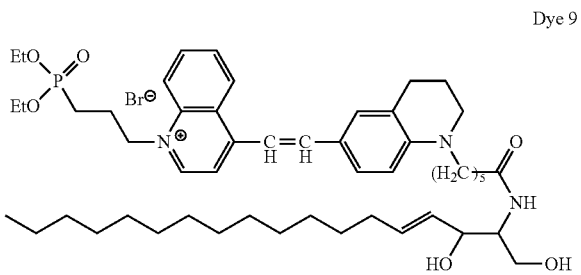

sphingosine conjugate

Example 11

Synthesis of Dye 10

(a) Preparation of Compound 14

A mixture of 15 g of 2-(methylthio)benzothiazole and 50 ml of chlorosulfonic acid was heated to 60° C. for 2 hours. After cooling to room temperature, the mixture was slowly added to 300 ml ice water with stirring. The white solid precipitate was collected by filtration and washed with water to give 14 g of Compound 14 whose structure is given below:

Compound 14

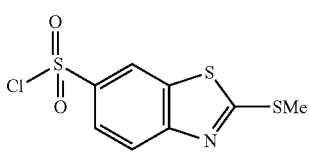

(b) Preparation of Compound 15

To a solution of 7.0 g of Compound 14 dissolved in 80 ml of dichloromethane, 8.1 ml of N,N,N'-Trimethylethylenediamine was slowly added and then the reaction mixture was stirred at room temperature overnight. The reaction mixture was shaken with 200 ml of water in a separation funnel followed by the aqueous layer being discarded. The reaction mixture was then shaken with 100 ml of brine and the organic solution was dried over MgSO$_4$. The solvent was removed by rotary evaporation and the solid residue was dried in vacuum to give 8.19 g of Compound 15 as white solid. The structure of Compound 15 is given below:

Compound 15

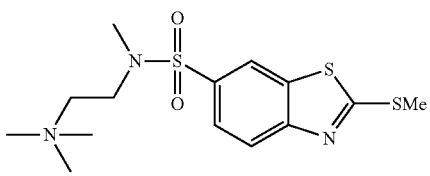

(c) Preparation of Compound 16

To 1.04 g of Compound 15, 1.6 ml of p-Toluenesulfonic acid methyl ester was added and the mixture was reacted at 130° C. for 4 hours. After cooling to room temperature, a resulting residue was washed with acetone and then ethyl acetate to give white solid. Drying the solid under vacuum yielded 2.02 g of Compound 16 whose structure is given below:

Compound 16

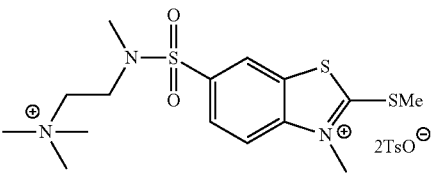

(d) Preparation of Compound 17

To 1.4 ml of lepidine 3.0 ml of p-Toluenesulfonic acid methyl ester was added and the mixture was reacted at 140° C. for 4 hours. After cooling to room temperature, a resulting residue was washed with acetone and then ethyl acetate to give light brown solid. Drying the solid under vacuum yielded 3.68 g of Compound 17 whose structure is given below:

Compound 17

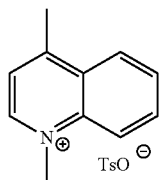

(e) Preparation of Dye 10

A mixture of 358 mg of Compound 16 and 177 mg of Compound 17 was suspended in 5 ml of ethanol. To this 91 µl of triethylamine was added and the mixture was refluxed for 1 hour. The solution was then cooled down to room temperature and added dropwise to cold ethyl acetate. Resulting orange precipitate was washed several times with ethyl acetate and dried under vacuum to provide Dye 10 whose structure is given below:

Dye 10

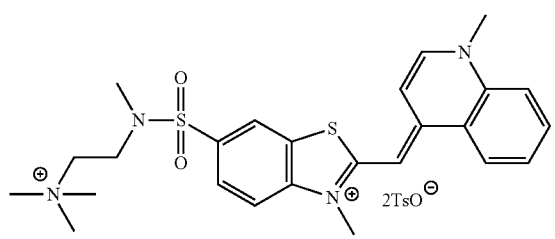

Example 12

Synthesis of Dye 11

(a) Preparation of Compound 18

To a solution of 13.2 g of Compound 14 dissolved in 150 ml of dichloromethane, 15 ml of piperidine was slowly added and then the reaction mixture was stirred at room temperature overnight. The reaction mixture was shaken with 50 ml of 2N HCl in a separation funnel followed by the aqueous layer being discarded. The reaction mixture was then shaken with 50 ml of saturated NaHCO$_3$ followed by the aqueous layer being discarded and the solution dried over MgSO$_4$. The organic solvent was removed by rotary evaporation and the solid residue Compound 18 was dried in vacuum. This product was used without further purification. The structure of Compound 18 is given below:

Compound 18

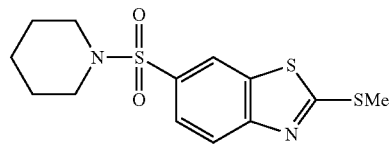

(b) Preparation of Compound 19

Compound 18 from step (a) was reacted with 50 ml p-Toluenesulfonic acid methyl ester at 140° C. for 2 hours. After cooling to room temperature, a precipitate formed which was collected by filtration and washed with 50 ml of acetone and 150 ml of ether to give 12 g of Compound 19 whose structure is given below:

Compound 19

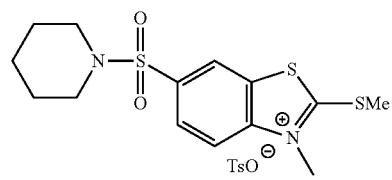

(c) Preparation of Dye 11

A mixture of 256 mg of Compound 19 and 180 mg of Compound 17 was suspended in 4 ml of ethanol. To the reaction mixture 76 µl of triethylamine was added and the mixture was refluxed for 1 hour. The solution was then cooled down to room temperature and added dropwise to cold ethyl acetate. Resulting orange precipitate was washed several times with ethyl acetate and dried under vacuum to give 190 mg of Dye 11 whose structure is given below:

Dye 11

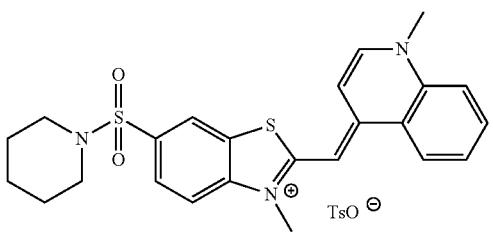

Example 13

Synthesis of Dye 12

(a) Preparation of Compound 20

To a solution of 1.4 mL of lepidine in 5 mL of dioxane, 5.8 ml of 1,3-diiodopropane was added. The reaction mixture was refluxed for 4 hours and then it was cooled to room temperature. Yellow precipitate formed was extensively washed with ethyl acetate and dried under vacuum to provide Compound 20 whose structure is given below:

Compound 20

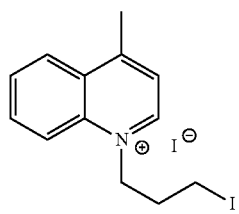

(b) Preparation of Compound 21

To 286 mg of Compound 16, 190 mg of Compound 20 was added and the mixture was suspended in 4 ml of ethanol. To the reaction mixture 72 µl of triethylamine was added and the mixture was refluxed for 1 hour. The solution was then cooled down to room temperature and added dropwise to cold ethyl acetate. Resulting orange-red precipitate was washed several times with ethyl acetate and dried under vacuum to provide Compound 21. The structure of Compound 21 is given below:

washed several times with ethyl acetate and dried under vacuum to provide Dye 13. The structure of the product is given below:

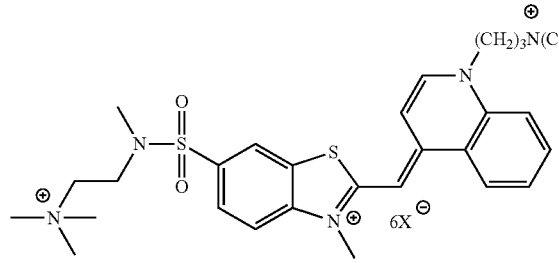

Compound 21

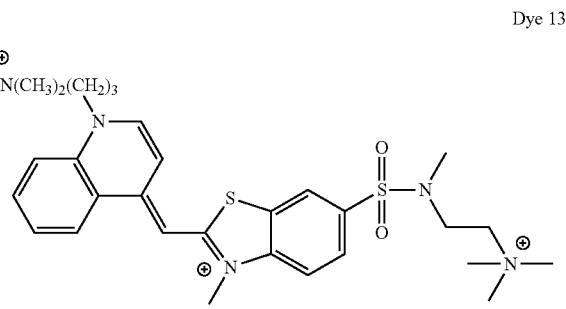

Dye 13

Example 15

Synthesis of Dye 14

(a) Preparation of Compound 22

To a solution of 1.32 ml of lepidine in 5 ml of dioxane, 0.75 ml of 1,6-diiodohexane was added. The reaction mixture was refluxed for 6 hours and then it was cooled to room temperature. Yellow precipitate was extensively washed with ethyl acetate and dried under vacuum to provide Compound 22 whose structure is given below:

(c) Preparation of Dye 12

To 30 mg of Compound 21 in 3 ml of dimethylformamide, 46 µl of N,N,N',N'-tetramethylpropylenediamine was added and the mixture was heated at 90° C. for 5 hours. The solution was then cooled down to room temperature and added dropwise to cold ethyl acetate. Resulting orange-red precipitate was washed several times with ethyl acetate and dried under vacuum to provide Dye 12 whose structure is given below:

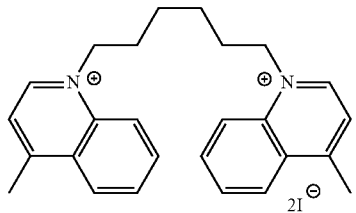

Compound 22

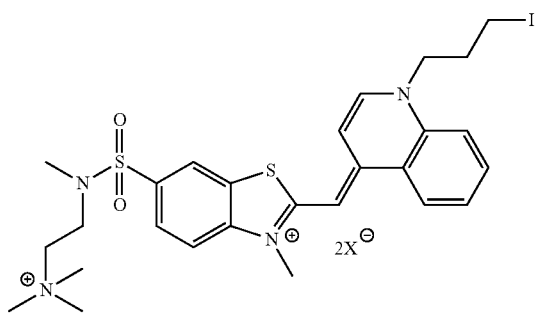

Dye 12

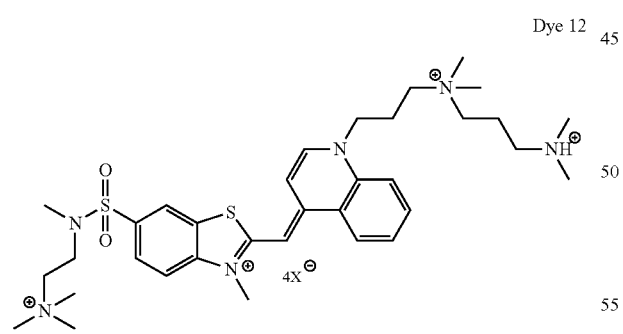

Example 14

Synthesis of Dye 13

To 102 mg of Compound 21 in 3 ml of dimethylformamide, 7.7 µl of N,N,N',N'-tetramethylpropylenediamine was added and the mixture was heated at 90° C. for 3 days. The solution was then cooled down to room temperature and added dropwise to ethyl acetate. Resulting orange-red precipitate was (b) Preparation of Dye 14

To 386 mg of Compound 19 [from step (b) of Example 12], 257 mg of Compound 22 was added and the mixture was suspended in 6 ml of ethanol. To the reaction mixture 115 µl of triethylamine was added and the mixture was refluxed for 1 hour. The solution was then cooled down to room temperature and added dropwise to ethyl acetate. Resulting red precipitate was washed several times with ethyl acetate and dried under vacuum to provide Dye 14 whose structure is given below:

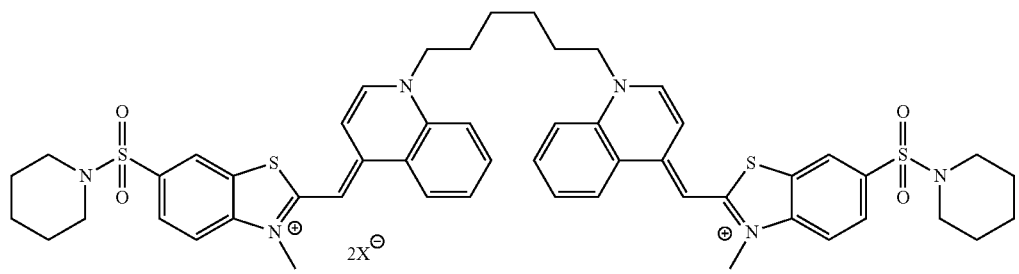

Dye 14

The following additional examples illustrate the use of the compounds described above.

Example 16

Nucleoli Staining with Dye 1

Figure 1B:
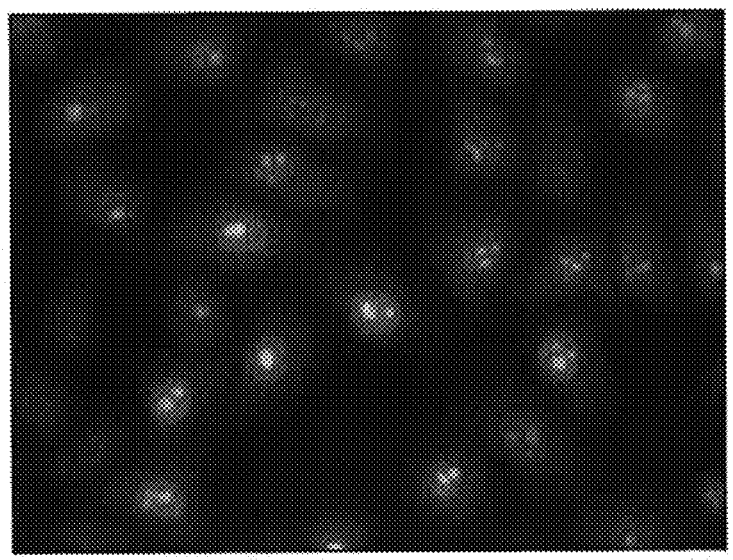

In this example, the nucleoli of HeLa human cervical carcinoma cell line were stained using Dye 1. HeLa cells were incubated with 15 μM of Dye 1 for 15 min at room temperature. As shown in FIG. 1, cells were imaged under bright field (top panel) and with a green FITC channel (bottom panel)

Example 17

Nuclei Staining with Dye 2

Figure 2A:
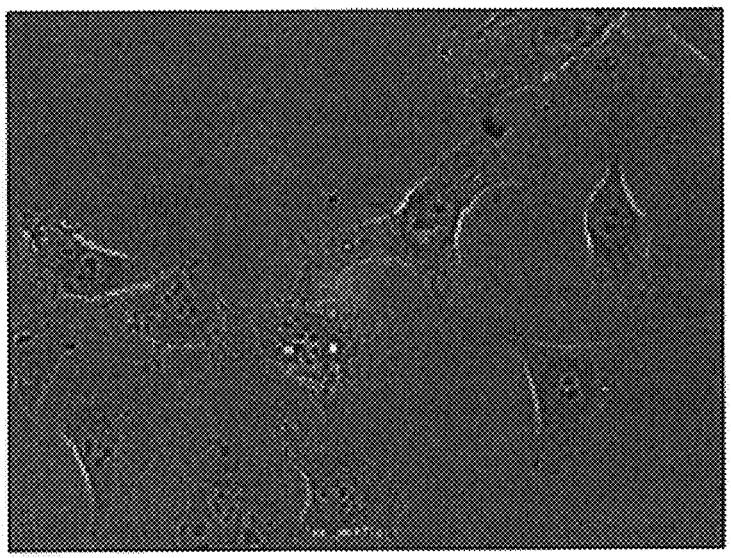
FIG. 2A-2B.
Figure 2B:
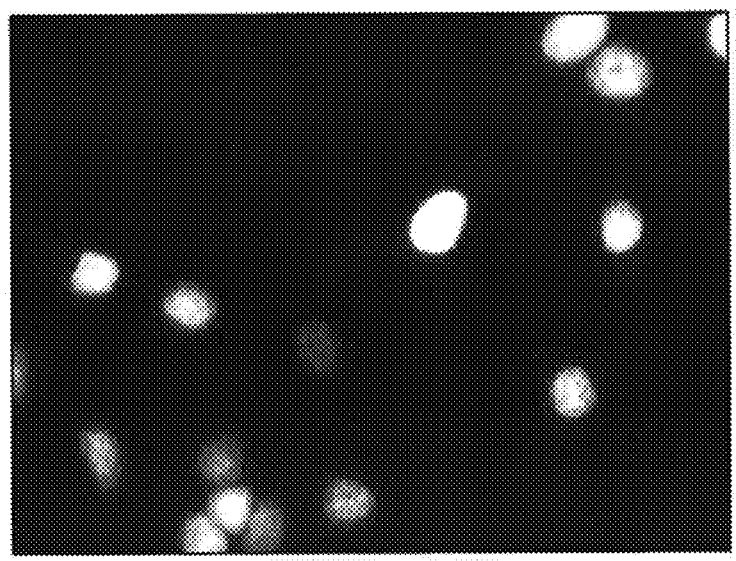

In this example, the nuclei of live HeLa human cervical carcinoma cells were stained with Dye 2. As in the previous example, HeLa cells were incubated with 10 μM of Dye 2 for 15 min at room temperature. The results are shown in FIG. 2. Cells were imaged under bright field (top panel) and with a Texas Red channel (bottom panel)

Example 18

Mitochondrial Staining with Dye 3

Figure 3A:
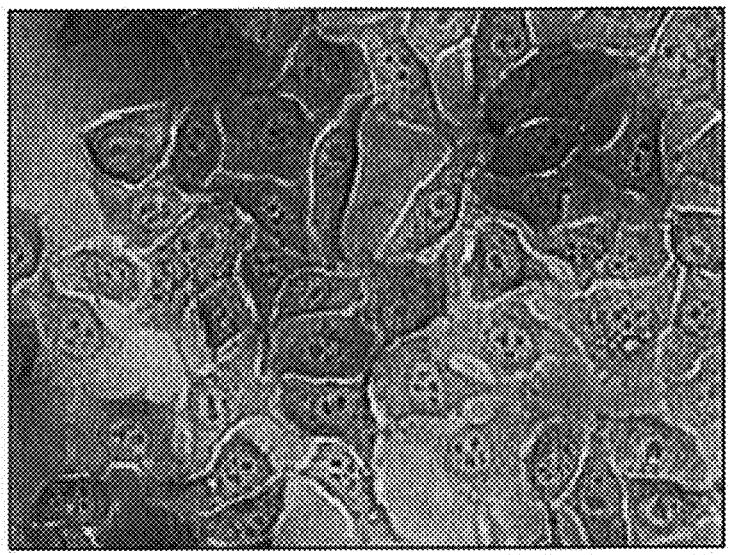
FIG. 3A-3B.
Figure 3B:
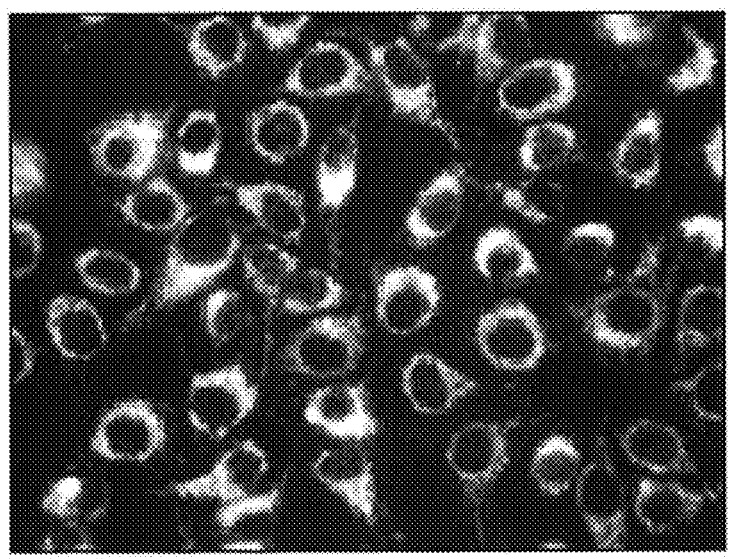

In this example, the mitochondria of live HeLa human cervical carcinoma cells were stained with Dye 3. HeLa cells were incubated with 80 μM of Dye 3 for 15 min at room temperature in a cover slip. The results of the staining are shown in FIG. 3. Cells were imaged under bright field (top panel) and with a Texas Red channel (bottom panel)

Example 19

Nuclei Staining with Dye 4

Figure 4A:
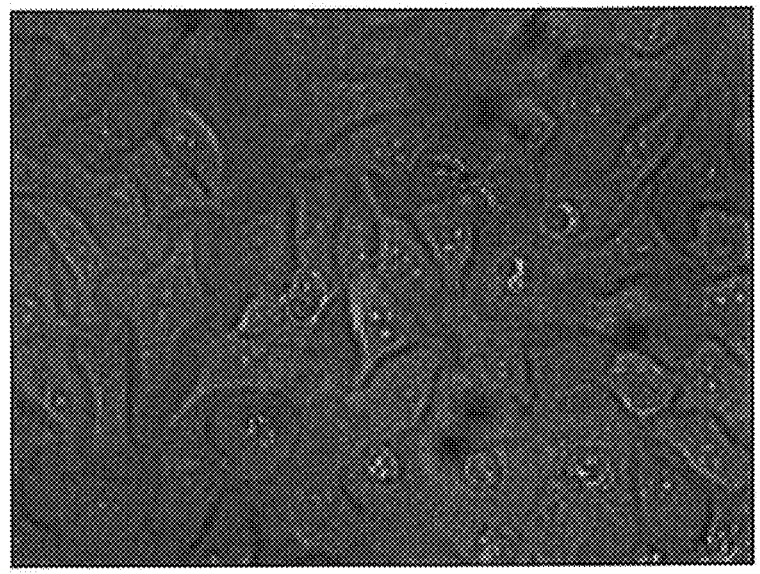
FIG. 4A-4B.
Figure 4B:
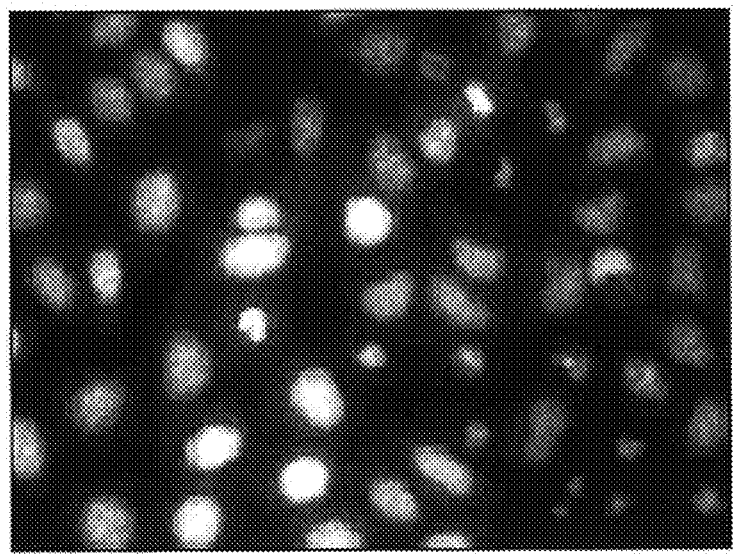

In this example, the nuclei of live HeLa human cervical carcinoma cells were stained with Dye 4. HeLa cells were incubated with 5 μM of Dye 4 for 15 min at room temperature. The results of the staining are shown in FIG. 4. Cells were imaged under bright field (top panel) and with a green FITC channel (bottom panel)

Example 20

Nucleoli Staining with Dye 5

Figure 5A:
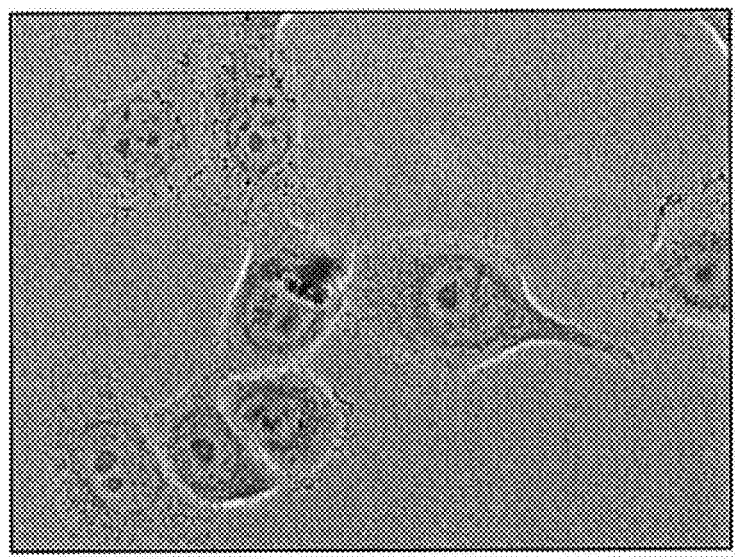
FIG. 5A-5B.
Figure 5B:
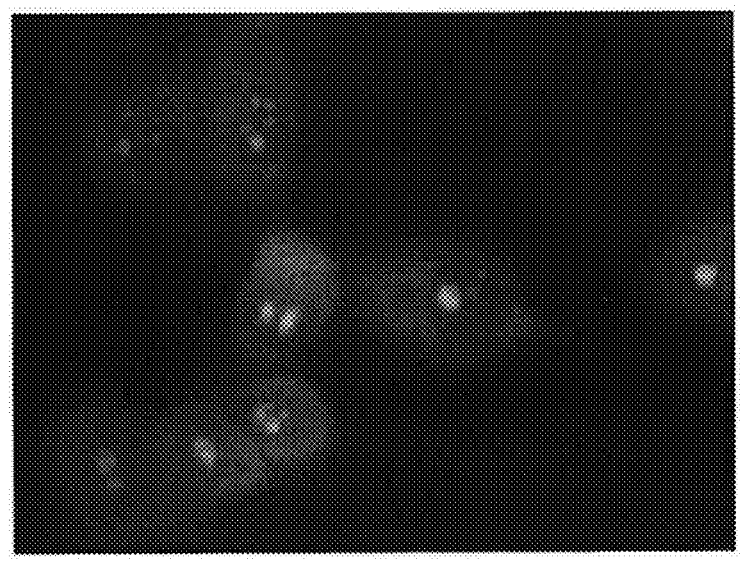

In this example, the nucleoli in HeLa human cervical carcinoma cell line were stained using Dye 5. HeLa cells were incubated with 10 μM of Dye 5 for 15 min at room temperature. The results of the staining are shown in FIG. 5. Cells were imaged under bright field (top panel) and with a DAPI channel (bottom panel)

Example 21

Nucleoli Staining with Dye 6

Figure 6A:
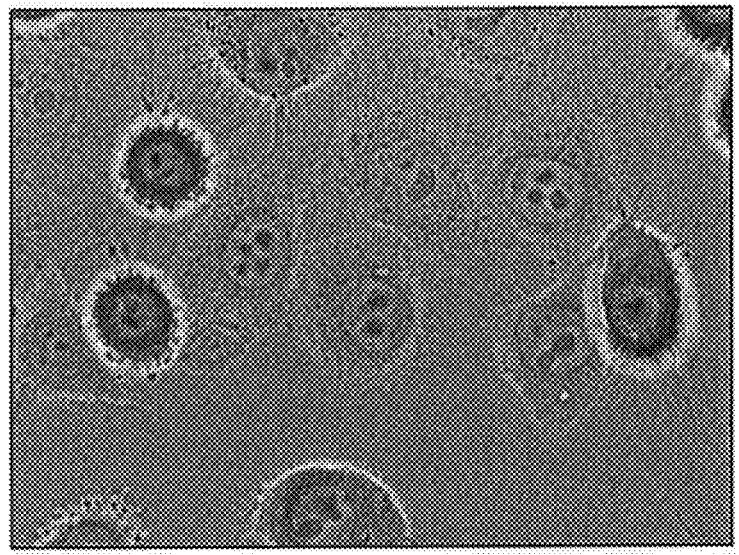
FIG. 6A-6B.
Figure 6B:
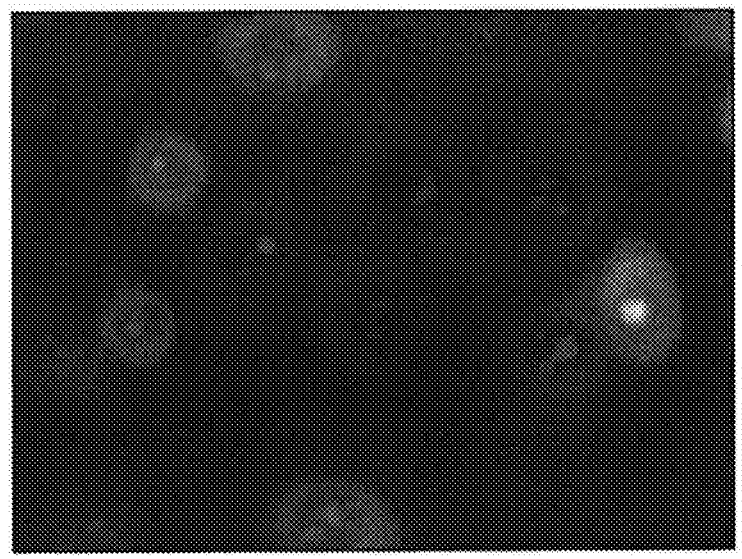

In this example, the nucleoli in HeLa human cervical carcinoma cell line were stained using Dye 6. HeLa cells were incubated with 10 μM of Dye 6 for 15 min at room temperature. The results of the staining are shown in FIG. 6. Cells were imaged under bright field (top panel) and with a DAPI channel (bottom panel)

Example 22

Nuclei Staining with Dye 7

Figure 7A:
FIG. 7A-7B.
Figure 7B:
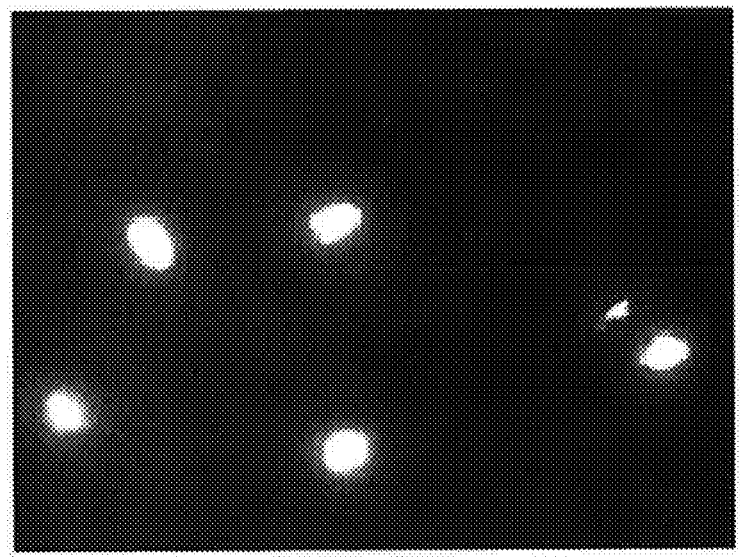

In this example, the nuclei of HeLa human cervical carcinoma cells were stained with Dye 7. HeLa cells were cultured on poly-lysine coated slides in DMEM medium containing FBS and Pen-strep. The cells were treated with 1 μM staurosporin for 4 h (to induce apoptosis). The medium was removed, cells washed and incubated with 5 μM of Dye 7 for 15 min at room temperature. The results of the staining are shown in FIG. 7. Cells were imaged under bright field (top panel) and with a Texas Red channel (bottom panel) to view staining of the nuclei of the dead cells.

Example 23

Cytoplasm Staining with Dye 8

Figure 8A:
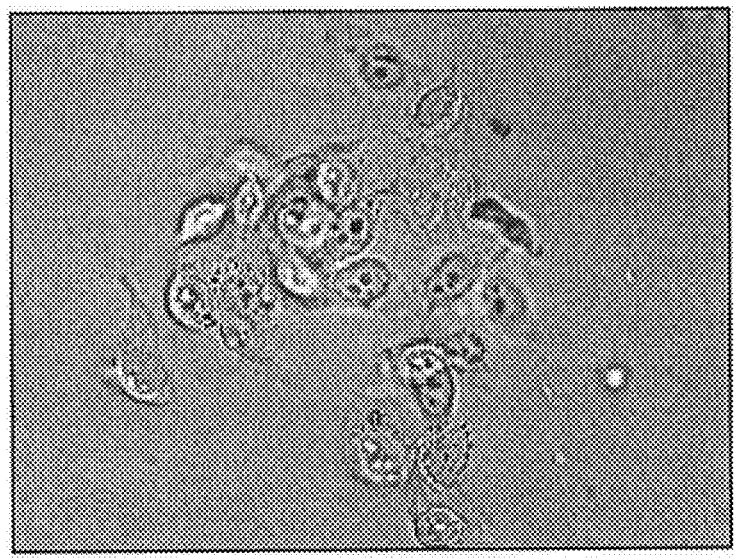
FIG. 8A-8B.
Figure 8B:
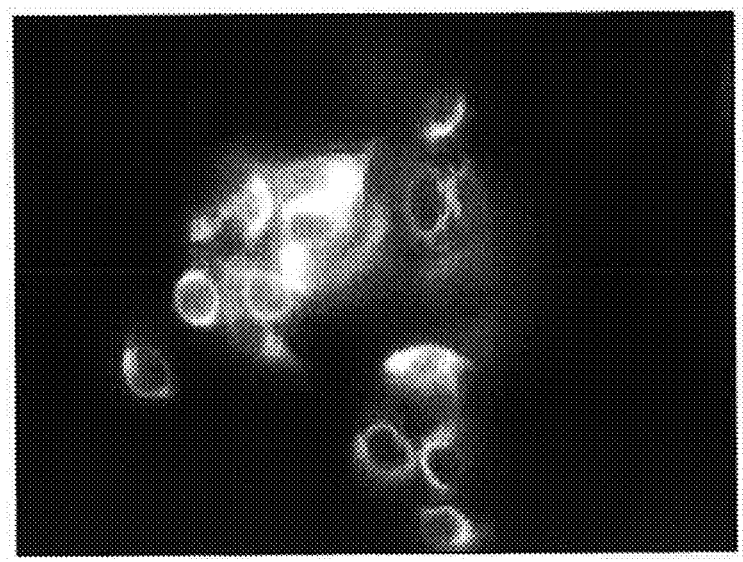

In this example, the cytoplasm of live HeLa human cervical carcinoma cells were stained with Dye 8. HeLa cells were incubated with 10 μM of Dye 8 for 15 min at room temperature. The results of the staining are shown in FIG. 8. Cells were imaged under bright field (top panel) and with a Texas Red channel (bottom panel).

Example 24

Golgi Bodies Staining with Dye9-Sphingosine Conjugate

Figure 9A:
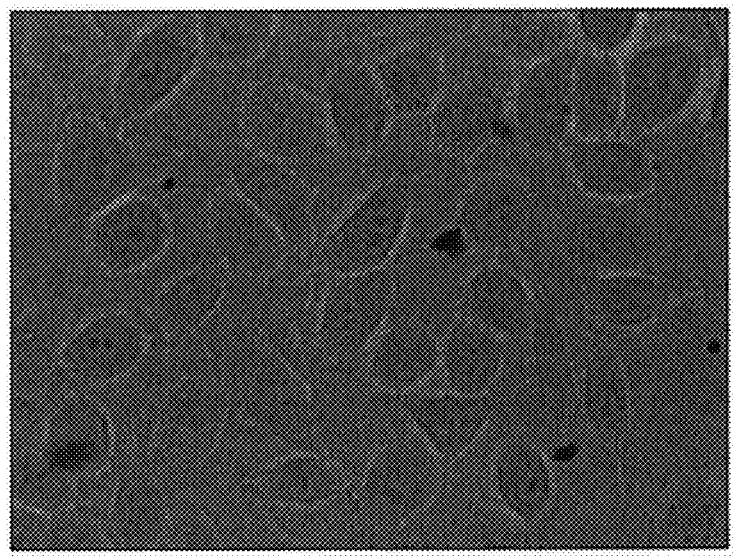
FIG. 9A-9B.
Figure 9B:
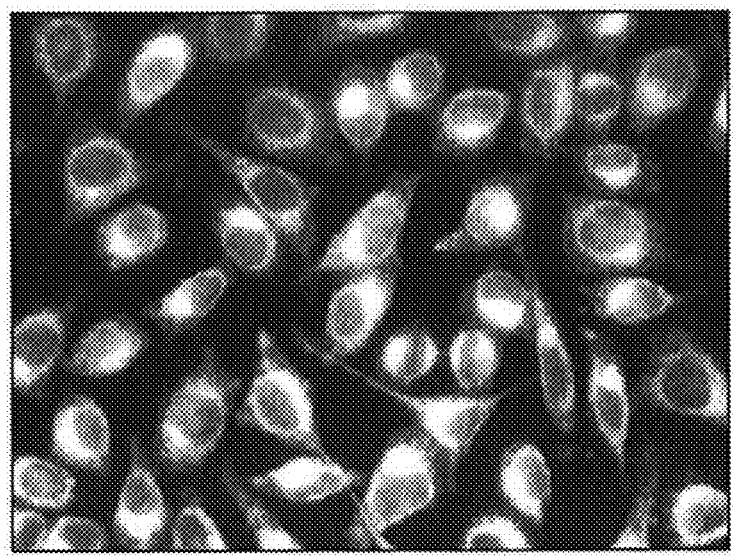

In this example, Golgi bodies of live HeLa human cervical carcinoma cells were stained with Dye 9-sphingosine conjugate. HeLa cells were incubated with 2.5 μM of Dye 9-ceramide for 15 min at room temperature. The results of the staining are shown in FIG. 9. Cells were imaged under bright field (top panel) and with a Texas Red channel (bottom panel).

Example 25

Interaction of Dyes 10-12 and 14 with Nucleic Acids

This example illustrates the interactions of Dyes 10-12 and 14 with nucleic acids. Dyes 10-12 and 14 have absorbance 494-500 nm and almost no fluorescence. The fluorescence intensity of the compounds, however, increases 150-500-fold upon binding to nucleic acids. The resulting dye-nucleic acid complexes absorb at 504-507 nm and emit at 522-530 nm. Additionally, some of the above stains show some selectivity towards either DNA (Dyes 11 and 14) or RNA (Dye 12).

For spectral properties determination, Dyes 10-12 and 14 were dissolved in DMSO and diluted with DMSO to give 1 mM stocks. The stocks were further diluted with water to concentration of 50 µM and they were incubated either with water alone or with water containing DNA (calf thymus) or RNA (*S. cerevisiae*). The final concentration of each dye and nucleic acid was 2.5:M and 100:g/ml, respectively. Fluorescence emission was measured with an excitation wavelength determined by measurement of dye-DNA/RNA complex absorbance.

The spectral properties of these four dyes (Dyes 10-12 and 14) upon binding to nucleic acids are shown in the Table 1 of FIG. 10.

Example 26

Staining with Dye 12

Figure 11A:
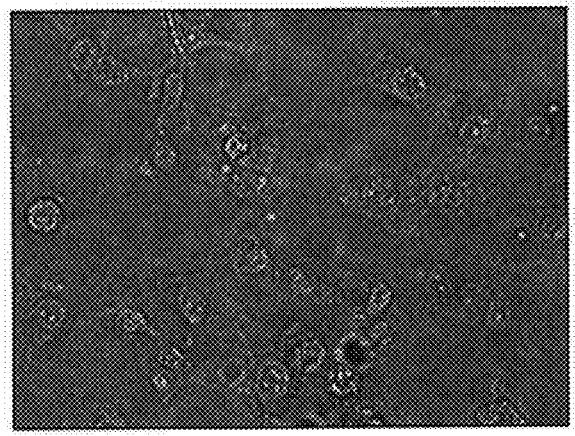
FIG. 11A-11C.
Figure 11B:
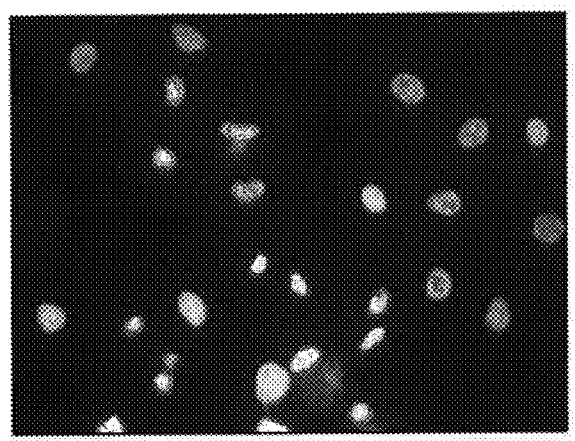
Figure 11C:
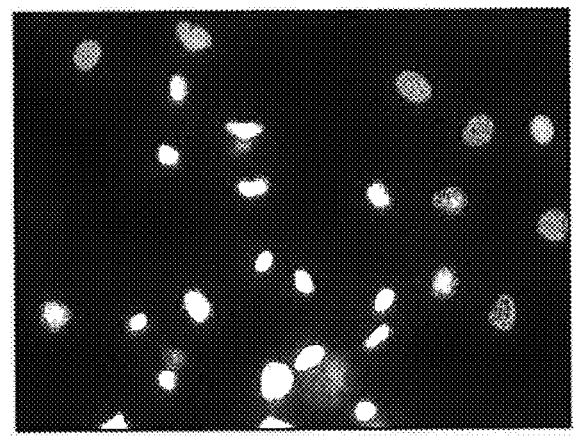

In this example, HeLa cells were stained with Dye 12. HeLa cells were cultured on poly-lysine coated slides in DMEM medium containing FBS and Pen-strep. The cells were treated with 1 µM staurosporin for 4 h. The medium was removed, cells washed and stained with 5 µM solution of Dye 12 in PBS for 15 minutes at room temperature. Extra staining solution was washed off and slides were coated with coverslips and viewed under microscope employing green filter. The results of the staining are shown in FIG. 11.

Example 27

Staining with Dyes 10-12 and 14

In this example, staining of HeLa cells was carried out using Dyes 10-12 and 14. HeLa cells were fixed on slides with methanol and then they were incubated with 2.5 µM solutions of Dyes 10-12 and 14 for 15 minutes. Extra staining solution was washed off and slides were coated with coverslips and viewed under microscope employing green filter.

Figure 12A:
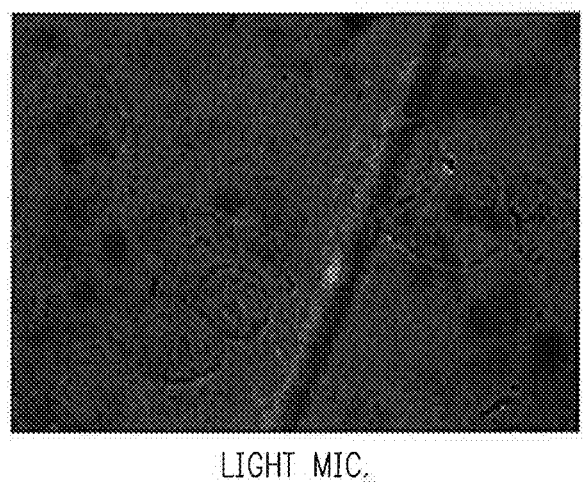
FIG. 12A-12C.
Figure 12B:
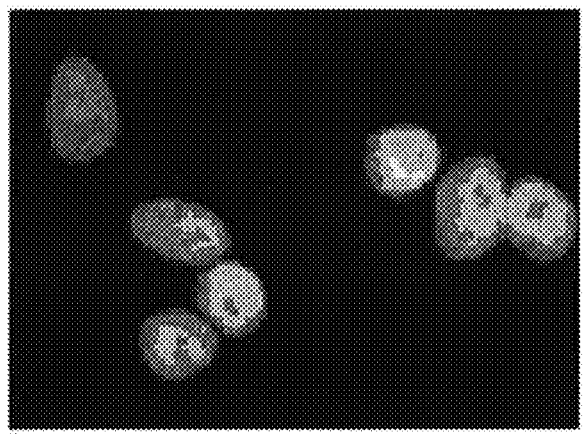
Figure 12C:
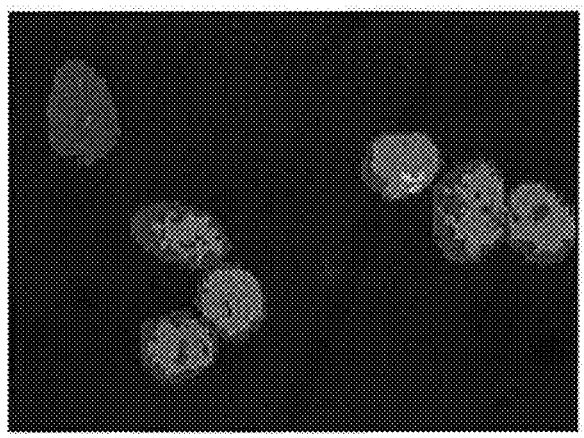

FIG. 12 shows micrographs with staining of fixed HeLa cells with Dye 12. a. Cells under light microscope; b. Cells viewed under microscope employing green filter; c. Composite of pictures a and b.

FIG. 13 provides Table 2 that shows the evaluation of these four dyes used for cell staining of the fixed HeLa cells. Table 2 shows the dye used and parameters of brightness, stability and selectivity.

Example 28

Electrophoresis Gel Staining with Dyes 10-12 and 14

In this example, Dyes 10-12 and 14 were examined with respect to their use in electrophoresis agarose gel staining. Due to strong affinity towards nucleic acids, Dyes 10-12 and 14 can be used for prestaining DNA before analysis by gel electrophoresis. Briefly, DNA ladder was prestained for 15 minutes with 10 µM solutions of Dyes 10-12 and 14. The samples were loaded and then run on Agarose precast gels.

Figure 14:
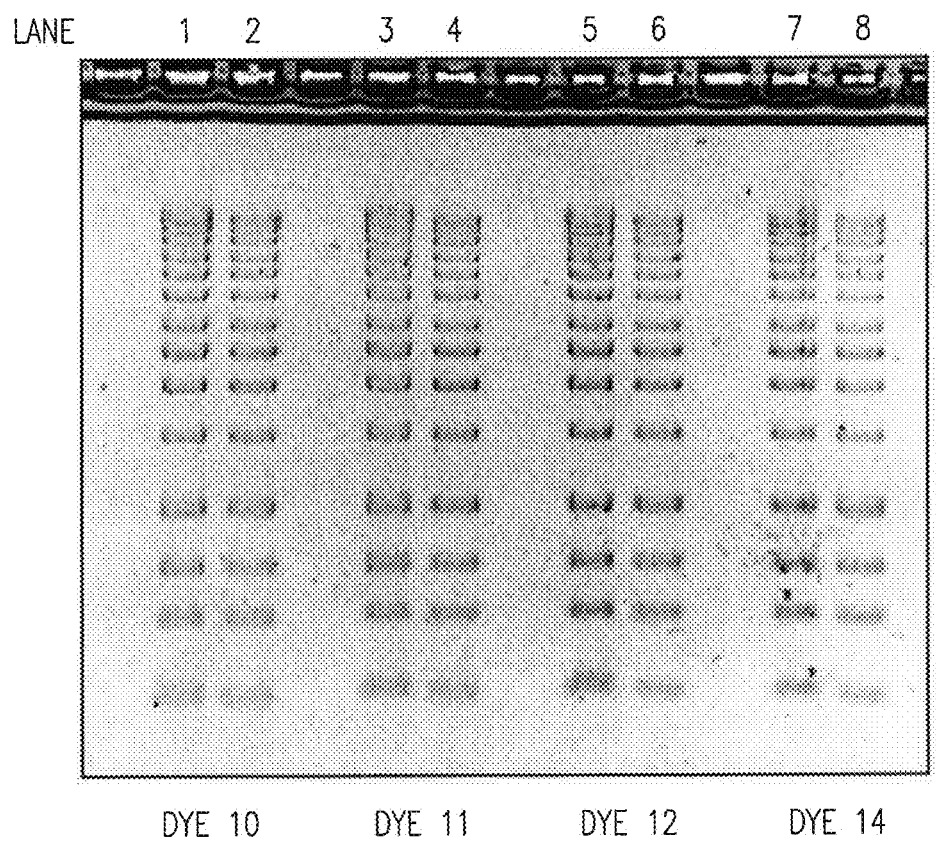
FIG. 14 is a photograph of an agarose gel that shows a DNA ladder obtained by prestaining DNA for 15 minutes with 10 μM solutions of Dyes 10-12 and 14.

The results of the staining and the gel electrophoretic analysis are shown in FIG. 14. Lanes 1 and 2 in the DNA ladder show Dye 10. Lanes 3 and 4 show Dye 11. Lanes 5 and 6 shows Dye 12 while lane 7 and 8 show Dye 14.

Many obvious variations will be suggested to those of ordinary skill in the art in light of the above detailed descriptions of the present invention. All such obvious variations are fully contemplated and are embraced by the scope and spirit of the present invention as set forth in the claims that now follow.

What is claimed is:

1. A compound having the structure:

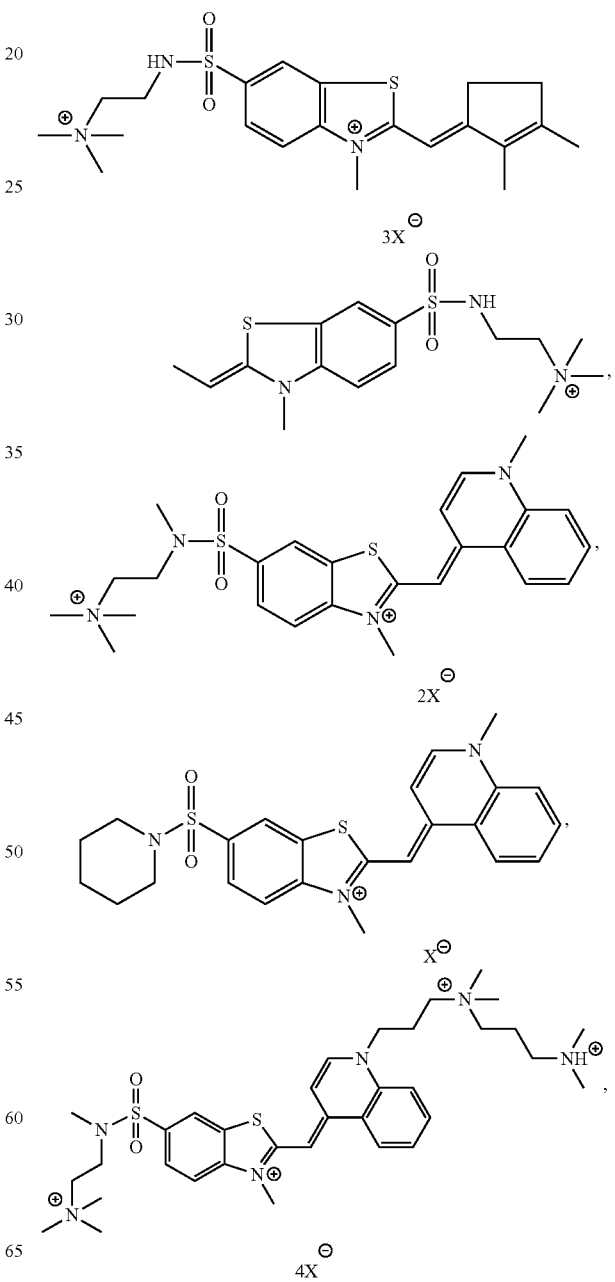

-continued
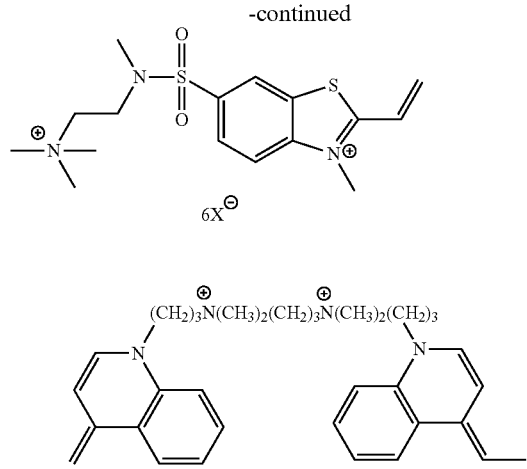
wherein X comprises an anion.
2. The compound of claim 1, having the structure:
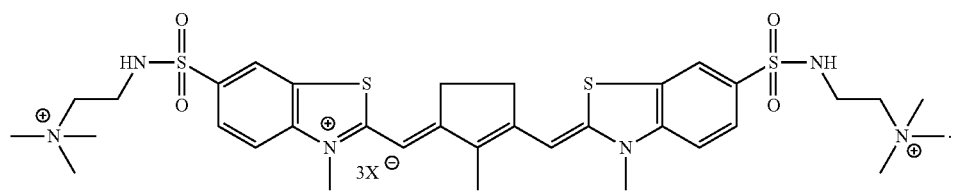
3. The compound of claim 1, having the structure:
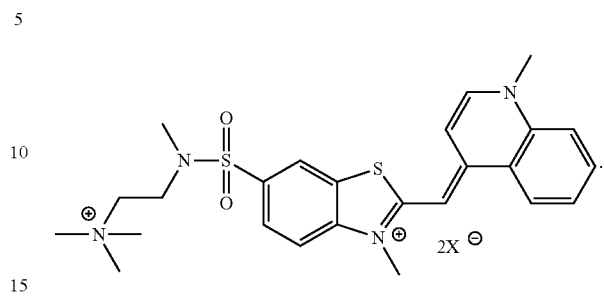
4. The compound of claim 1, having the structure:
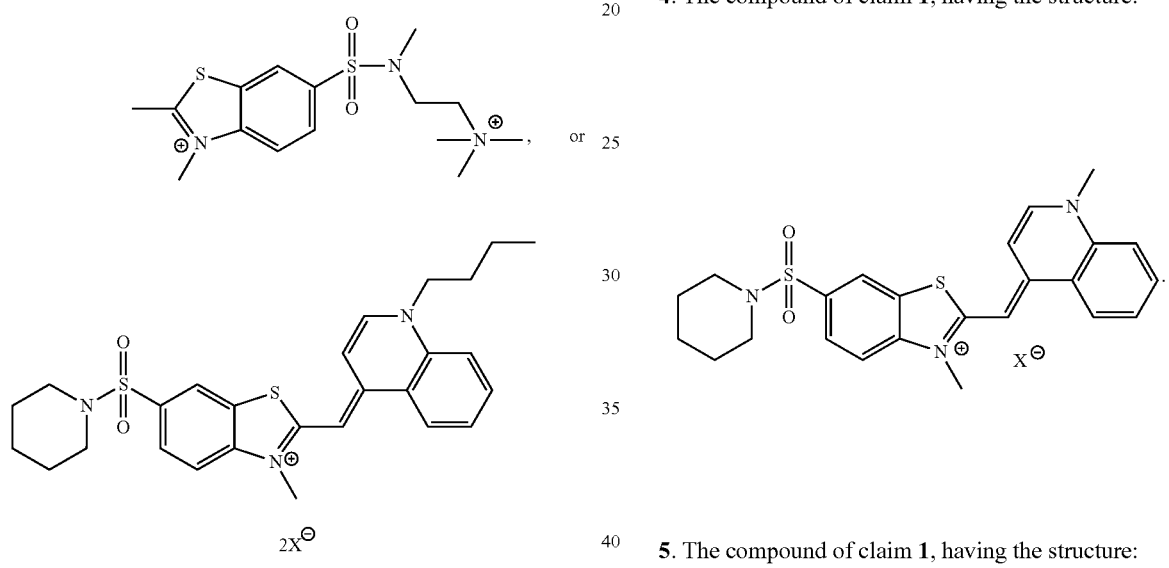
5. The compound of claim 1, having the structure:
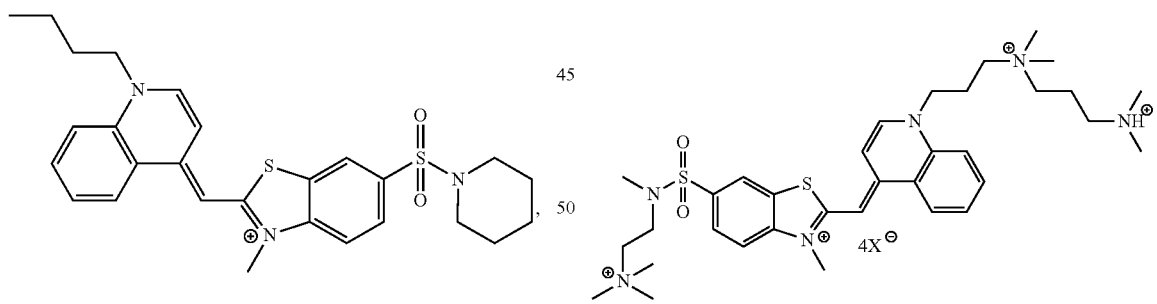

6. The compound of claim 1, having the structure:

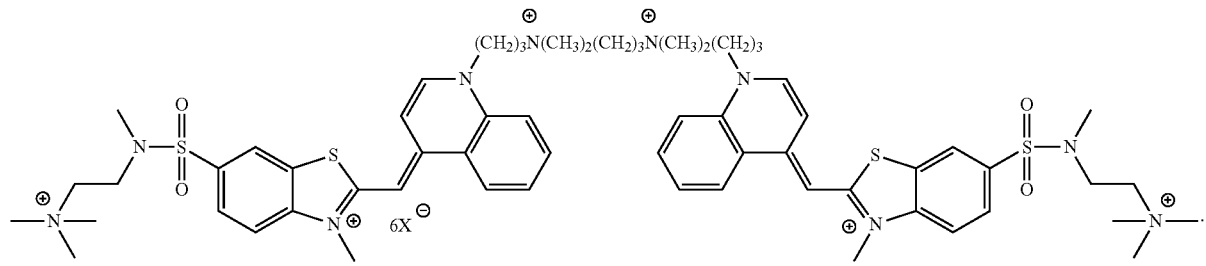

7. The compound of claim 1, having the structure:

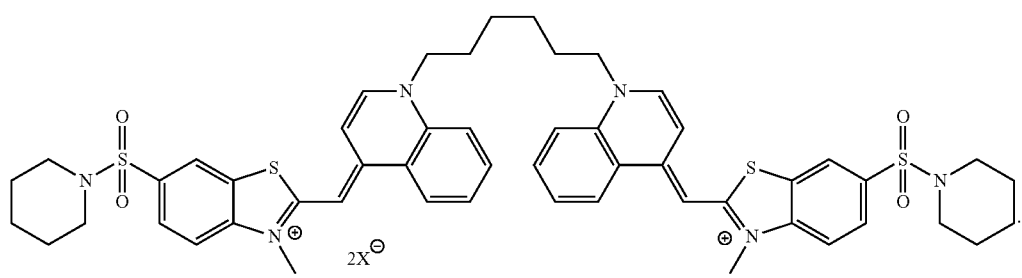 [SMILES: C[n+]1c(/C=C2\C=CN(CCCCCCN3C=C/C(=C\c4sc5cc(S(=O)(=O)N6CCCCC6)ccc5[n+]4C)c4ccccc43)c3ccccc32)sc2cc(S(=O)(=O)N3CCCCC3)ccc21]

8. A method of identifying a specific organelle or region in a cell of interest, the method comprising
   (a) incubating the cell of interest with the compound of claim 1, and
   (b) identifying the location of the organelle or region in the cell of interest by identifying the compound that stains the organelle or region.

9. The method of claim 8, wherein the compound is

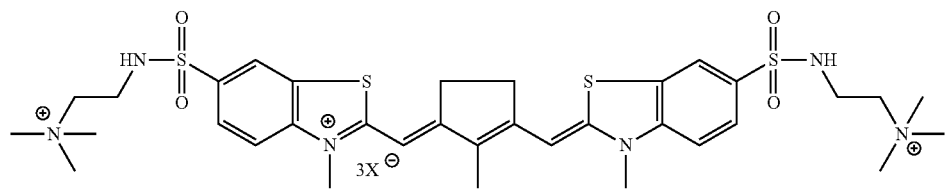

and the organelle or region is a nucleus.

10. A target molecule comprising the compound of claim 1.

11. The target molecule of claim 10, wherein the target molecule is a nucleoside, a nucleotide, an oligonucleotide, a polynucleotide, a peptide nucleic acid, a protein, an oligopeptide, an enzyme, an antibody, a cytokine, avidin, streptavidin, digoxigenin, an oligosaccharide, a polysaccharide, a lipid, a liposome, a glycolipid, or a dye.

12. The target molecule of claim 10, wherein the target molecule is a protein, an oligopeptide, a nucleotide, an oligonucleotide, or a polynucleotide.

13. A compound having the structure:

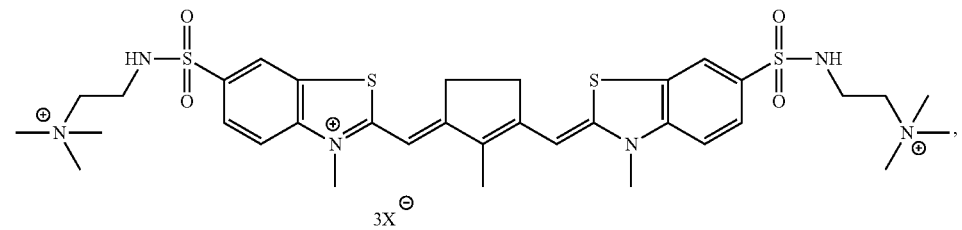

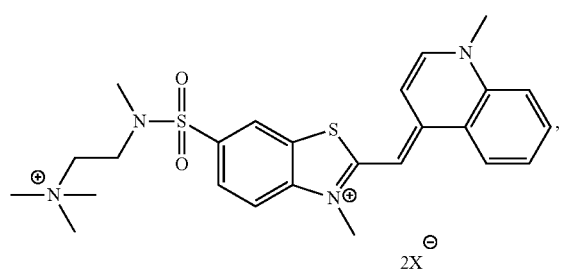
2X⁻
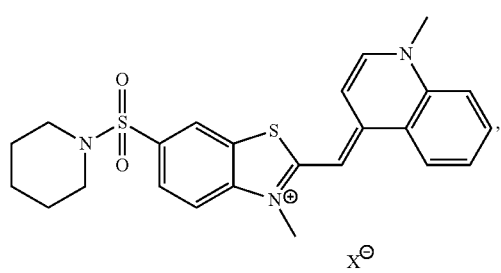
X⁻
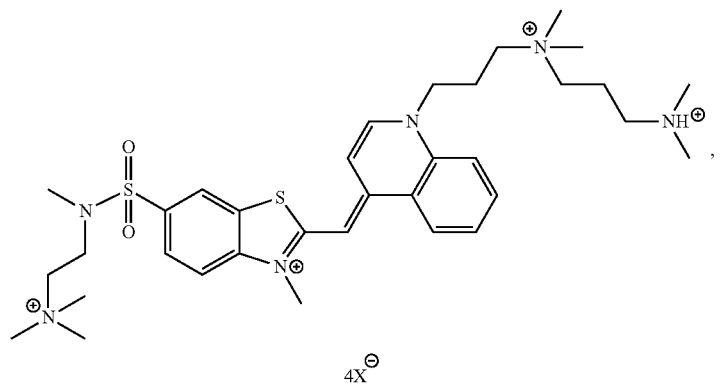
4X⁻
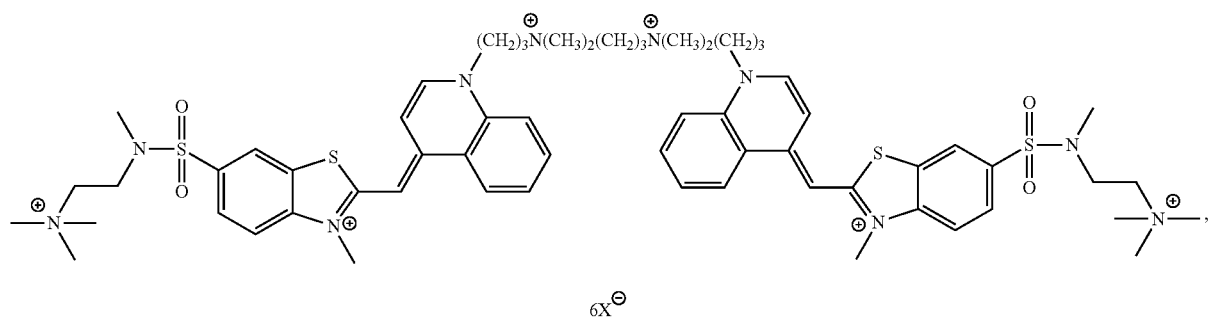
6X⁻
or
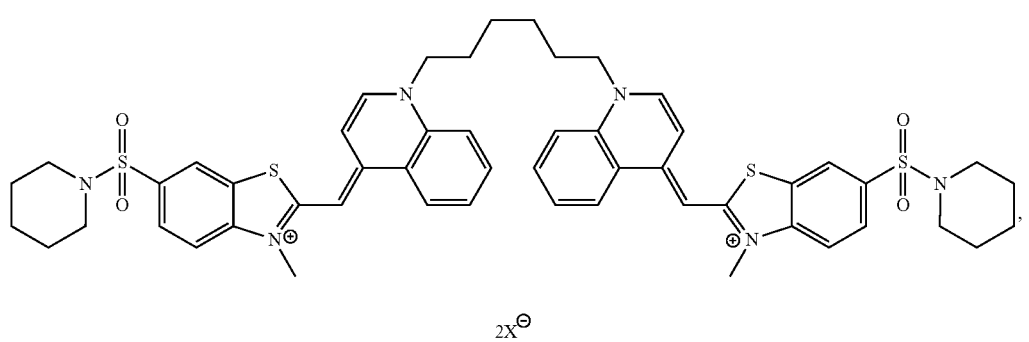
2X⁻ wherein X comprises an anion and wherein the compound also has at least one reactive group.

14. The compound of claim 13, wherein said reactive group comprises a nucleophilic reactive group, an electrophilic reactive group, a terminal alkene, a terminal alkyne, a coordinate group or an alkylating agent.

15. The compound of claim 13, wherein said reactive group comprises a nucleophilic reactive group comprising a thiol, amine or hydroxyl group.

16. The compound of claim 13, wherein said reactive group comprises a electrophilic reactive group comprising an isocyanate, isothiocyanate, monochlorotriazine, dichlorotriazine, 4,6,-dichloro-1,3,5-triazines, mono- or di-halogen substituted pyridine, mono- or di-halogen substituted diazine, maleimide, haloacetamide, aziridine, sulfonyl halide, acid halide, hydroxysuccinimide ester, hydroxysulfosuccinimide ester, imido ester, hydrazine, azidonitrophenol, azide, 3-(2-pyridyl dithio)-proprionamide, glyoxal or aldehyde group.

17. A method of labeling a target molecule, the method comprising attaching the compound of claim 13 to the target molecule by means of the reactive group, thereby labeling the target molecule.

18. The method of claim 17, wherein said reactive group comprises a nucleophilic reactive group, an electrophilic reactive group, a terminal alkene, a terminal alkyne, a coordinate group or an alkylating agent.

19. The method of claim 17, wherein said reactive group comprises a thiol, an amine or a hydroxyl group.

20. The method of claim 17, wherein said reactive group comprises an isocyanate, isothiocyanate, monochlorotriazine, dichlorotriazine, 4,6,-dichloro-1,3,5-triazines, mono- or di-halogen substituted pyridine, mono- or di-halogen substituted diazine, maleimide, haloacetamide, aziridine, sulfonyl halide, acid halide, hydroxysuccinimide ester, hydroxysulfosuccinimide ester, imido ester, hydrazine, azidonitrophenol, azide, 3-(2-pyridyl dithio)-proprionamide, glyoxal or aldehyde group.

* * * * *